US012749583B2

(12) United States Patent
Miesse et al.

(10) Patent No.: US 12,749,583 B2
(45) Date of Patent: Sep. 29, 2026

(54) SYSTEMS AND METHODS FOR MACHINE LEARNING CONTROL OF A SURGICAL DEVICE

(71) Applicant: Covidien LP, Mansfield, MA (US)

(72) Inventors: Andrew M. Miesse, North Haven, CT (US); Binesh Kumar Sadanandan, North Haven, CT (US); Christopher K. Evans, North Haven, CT (US); Robert H Knapp, North Haven, CT (US); Neethu Lekshmi Vasudevan Jalaja, Minneapolis, MN (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/866,693

(22) PCT Filed: May 18, 2023

(86) PCT No.: PCT/IB2023/055128
§ 371 (c)(1),
(2) Date: Nov. 18, 2024

(87) PCT Pub. No.: WO2023/223258
PCT Pub. Date: Nov. 23, 2023

(65) Prior Publication Data

US 2025/0322952 A1 Oct. 16, 2025

Related U.S. Application Data

(60) Provisional application No. 63/344,184, filed on May 20, 2022.

(51) Int. Cl.
*A61B 17/072* (2006.01)
*G16H 40/63* (2018.01)
(Continued)

(52) U.S. Cl.
CPC ....... *G16H 50/20* (2018.01); *A61B 17/07207* (2013.01); *G16H 40/63* (2018.01);
(Continued)

(58) Field of Classification Search
CPC .... A61B 17/07207; A61B 2017/00017; A61B 2017/00022; A61B 2017/00398;
(Continued)

(56) References Cited

U.S. PATENT DOCUMENTS

2010/0128941 A1 5/2010 Yang
2012/0116416 A1 5/2012 Neff et al.
(Continued)

FOREIGN PATENT DOCUMENTS

WO WO-2023029497 A1 * 3/2023 ... A61B 2017/00022

OTHER PUBLICATIONS

PCT/IB2023/055128, PCT International Search Report and Written Opinion, mailed Dec. 13, 2023, 21pages.

*Primary Examiner* — Linda J. Hodge

(57) ABSTRACT

A computer-implemented method for control of a surgical device includes accessing raw data captured by a sensor of the surgical device during a procedure, filtering the raw data with a filter, generating a difference data based on a difference between the raw data and the filtered data, generating zero-crossing data based on determining a point in time where an amplitude of the difference data last crossed from a non-zero amplitude value through a zero amplitude value to a non-zero amplitude value of the opposite sign, providing the zero-crossing data as an input to a machine learning classifier, and predicting a probability of an end stop point based on the machine learning classifier. The end stop point includes a point in time where a knife of the surgical device ceases to cut tissue.

14 Claims, 19 Drawing Sheets

(51) Int. Cl.
*G16H 50/20* (2018.01)
*A61B 17/00* (2006.01)

(52) U.S. Cl.
CPC ............... *A61B 2017/00022* (2013.01); *A61B 2017/00398* (2013.01); *A61B 2017/07271* (2013.01); *A61B 2017/07278* (2013.01); *A61B 2017/07285* (2013.01)

(58) Field of Classification Search
CPC A61B 2017/07271; A61B 2017/07278; A61B 2017/07285; A61B 34/00; A61B 34/30; G16H 50/20; G16H 40/63
USPC ........................................................ 227/180.1
See application file for complete search history.

(56) References Cited

U.S. PATENT DOCUMENTS

| | | | |
|---|---|---|---|
| 2019/0201081 A1 | 7/2019 | Shelton et al. | |
| 2021/0196269 A1 * | 7/2021 | Shelton, IV | H05K 1/147 |
| 2024/0161497 A1 * | 5/2024 | Luengo Muntion | G06N 3/0475 |
| 2025/0336512 A1 * | 10/2025 | Shelton, IV | H03K 17/9535 |

* cited by examiner

SYSTEMS AND METHODS FOR MACHINE LEARNING CONTROL OF A SURGICAL DEVICE

CROSS-REFERENCE TO RELATED APPLICATIONS

This application is a National Stage Application of PCT/IB2023/055128 filed May 18, 2023, which claims benefit of and priority to U.S. Provisional Application No. 63/344,184 filed May 20, 2022, and the disclosures of each of the above-identified applications are hereby incorporated by reference in their entirety.

TECHNICAL FIELD

The present disclosure relates to surgical devices. More specifically, the present disclosure relates to handheld electromechanical surgical systems for performing surgical procedures.

BACKGROUND

One type of surgical device is a linear clamping, cutting, and stapling device. Such a device may be employed in a surgical procedure to resect a cancerous or anomalous tissue from a gastro-intestinal tract. Conventional linear clamping, cutting, and stapling instruments include a pistol grip-styled structure having an elongated shaft and distal portion. The distal portion includes a pair of scissors-styled gripping elements, which clamp tissue, e.g., the open ends of tubular tissue. In this device, one of the two scissors-styled gripping elements, such as the anvil portion, moves or pivots relative to the overall structure, whereas the other gripping element remains fixed relative to the overall structure. The actuation of this scissoring device (the pivoting of the anvil portion) is controlled by a grip trigger maintained in the handle.

In addition to the scissoring device, the distal portion also includes a stapling mechanism. The fixed gripping element of the scissoring mechanism includes a staple cartridge receiving region and a mechanism for driving the staples up through the clamped end of the tubular tissue tissue against the anvil portion, thereby sealing the previously opened end. The scissoring elements may be integrally formed with the shaft or may be detachable such that various scissoring and stapling elements may be interchangeable.

In a manual surgical device, the user is required to use two hands to position the stapler in the desired articulation position. The user is also required to squeeze and release a handle multiple times (depending on the length of the loading unit) to clamp the loading unit, and to advance the knife along the loading unit. When an end stop point is reached, the handle can no longer be squeezed. After firing is complete, a second hand is often again required to retract the knife and unclamp the stapled tissue.

Advanced technology and informatics within these intelligent battery-powered stapling devices provide the ability to gather clinical data and drive design improvements to improve patient outcomes. However, a need still exists to better evaluate conditions that affect staple formation and knife movement to build a more intelligent stapling algorithm.

SUMMARY

In one aspect of the present disclosure, a computer-implemented method for control of a surgical device is presented. The computer-implemented method includes accessing raw data captured by a sensor of the surgical device during a procedure, and filtering the data with a filter. The filter includes a moving minimum filter. The method further includes generating a difference data based on a difference between the raw data and the filtered data, generating zero-crossing data based on determining a point in time where an amplitude of the difference data last crossed from a non-zero amplitude value through a zero amplitude value to a non-zero amplitude value of the opposite sign, providing the zero-crossing data as an input to a machine learning classifier, and predicting a probability of an end stop point based on the machine learning classifier. The end stop point may include a point in time where a knife of the surgical device ceases to cut tissue.

In some aspects, the raw data may include one or more pulse width modulated (PWM) signals configured to control a motor of the surgical device.

In some aspects, the method may further include controlling the motor to prevent further movement of the knife.

In some aspects, the difference data may include time-series data.

In some aspects, the method may further include determining at least one of a safety or efficacy of an end effector of the surgical device based on the predicted probability.

In some aspects, the method may further include determining if staples are formed based on the predicted end stop point probability.

In some aspects, the method may further include determining a presence of a sled of the surgical device based on the predicted end stop point probability.

In some aspects, the method may further include processing the raw data to determine a root means square value, a shape factor, and/or a crest factor of the raw data; and inputting to the machine learning classifier the determined the root means square value, the shape factor, and/or the crest factor of the raw data.

In some aspects, the machine learning classifier may include a decision tree.

In one aspect of the present disclosure, a system for control of a surgical device is presented. The system includes a surgical stapling device, including a sensor configured to sense a signal, the signal configured to control a motor of the surgical stapling device. The surgical stapling device includes at least one processor and at least one memory. The at least one memory includes instructions stored thereon, which, when executed by the at least one processor, cause the system to access raw data captured by the sensor of the surgical device during a procedure; filter the raw data, the filter including a moving minimum filter; generate a difference data based on a difference between the raw data and the filtered data; generate zero-crossing data based on determining a point in time where an amplitude of the difference data last crossed from a non-zero amplitude value through a zero amplitude value to a non-zero amplitude value of the opposite sign; input the zero-crossing data to a machine learning classifier; and predict a probability of an end stop point based on the machine learning classifier, wherein the end stop point includes a point in time where the knife of the surgical device ceases to cut tissue.

In some aspects, the surgical stapling device may further include a knife configured to cut tissue and a motor configured to advance the knife. The raw data may include a pulse width modulated signal configured to control the motor of the surgical stapling device.

In some aspects, the instructions, when executed by the at least one processor, may further cause the system to determine a safety and/or efficacy of an end effector of the surgical stapling device based on the predicted probability.

In some aspects, the instructions, when executed by the at least one processor, may further cause the system to determine if staples of the surgical stapling device are formed based on the predicted end stop point probability.

In some aspects, the instructions when executed by the at least one processor may further cause the system to process the raw data to determine a root means square value, a shape factor, and/or a crest factor of the signal; and input to the machine learning classifier, the determined root means square value, shape factor, and/or crest factor of the signal.

In one aspect of the present disclosure, a computer-implemented method for control of a surgical device includes accessing raw data captured by a sensor of the surgical device during a procedure; selecting a window of the raw data, wherein the window is configured to make the raw data non-periodic; extracting a feature from the windowed data; inputting the extracted feature to a machine learning classifier; and predicting a probability of a presence of a sled of the surgical device based on the machine learning classifier. The sensor includes an ammeter, accelerometer, inertial measurement unit, and/or a strain gauge.

In some aspects, the extracted feature may include an average current of a motor of the surgical device and/or a force imparted on the motor.

In some aspects, the raw data may include timeseries data.

In some aspects, the method may further include determining at least one of a safety or efficacy of an end effector of the surgical device based on the predicted probability.

In some aspects, the method may further include determining a probability that staples of the surgical device are formed based on the predicted probability.

In some aspects, the method may further include determining the presence of a sled of the surgical device based on the predicted probability, and in a case that a sled is not determined to be present, disabling firing of the surgical device.

BRIEF DESCRIPTION OF THE DRAWINGS

The present disclosure relates to surgical devices. More specifically, the present disclosure relates to handheld electromechanical surgical systems for performing surgical procedures.

Figure 1:
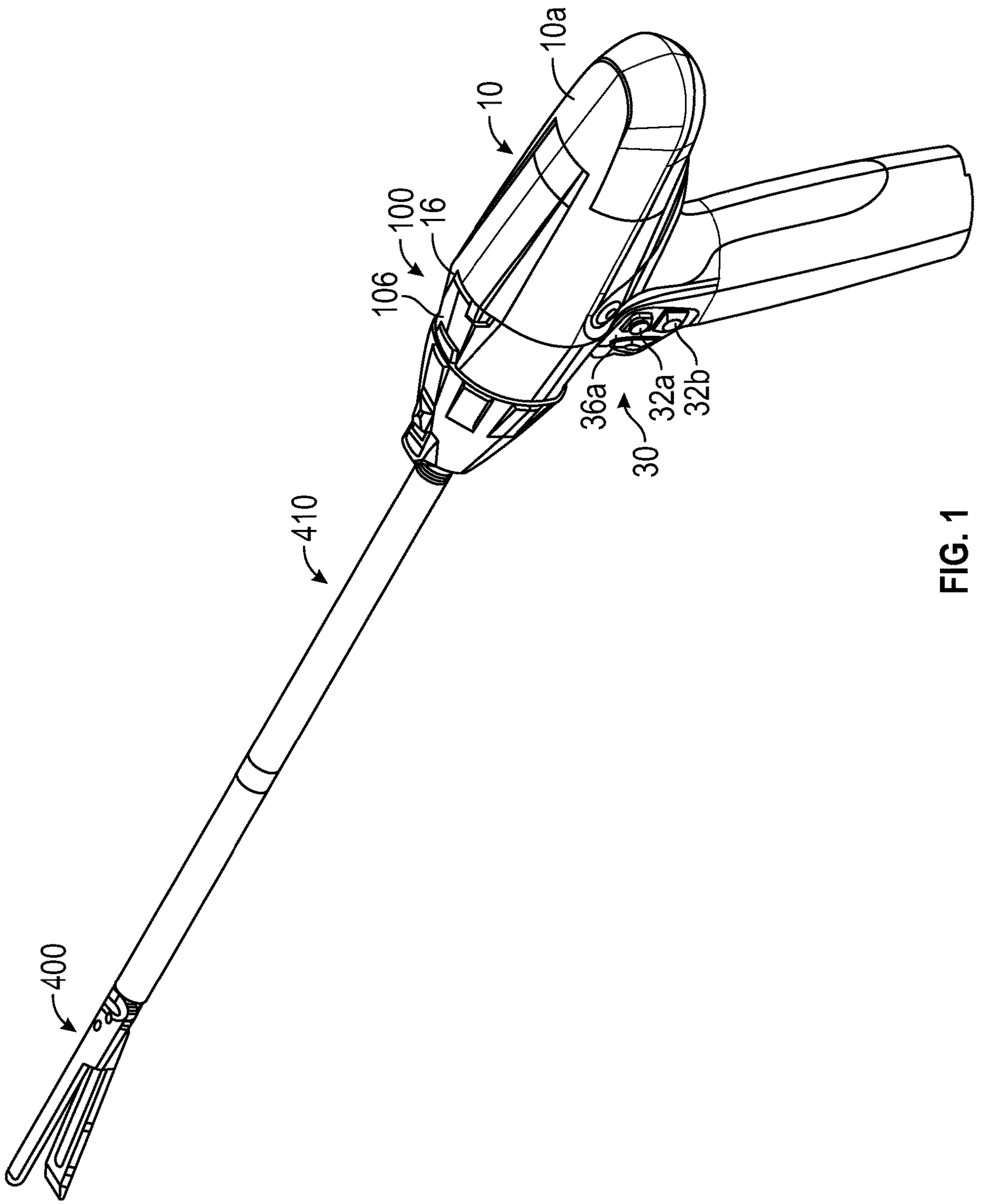
FIG. 1 is a perspective view of a handheld surgical device and adapter assembly, in accordance with an aspect of the present disclosure, illustrating a connection thereof with an end effector.

The details of one or more aspects of the disclosure are set forth in the accompanying drawings and the description below. Other features, objects, and advantages of the techniques described in this disclosure will be apparent from the description and drawings, and from the claims that follow.

DETAILED DESCRIPTION

Aspects of the presently disclosed surgical devices, and adapter assemblies for surgical devices and/or handle assemblies are described in detail with reference to the drawings, in which like reference numerals designate identical or corresponding elements in each of the several views. As used herein the term “distal” refers to that portion of the adapter assembly or surgical device, or component thereof, farther from the user, while the term “proximal” refers to that portion of the adapter assembly or surgical device, or component thereof, closer to the user. The term “clinician” refers to a doctor, nurse, or other care provider and may include support personnel.

A surgical device, in accordance with an aspect of the present disclosure, is designated as 100, and is in the form of a powered handheld electromechanical instrument configured for selective attachment thereto of a plurality of different end effectors that are each configured for actuation and manipulation by the powered hand held electromechanical surgical instrument. In addition to enabling powered actuation and manipulation, surgical device 100 further incorporates various safety and control features that help ensure proper, safe, and effective use thereof.

The systems and methods described herein utilize various surgical device parameters, such as motor current, to train a machine learning classifier for control of the surgical device.

As illustrated in FIG. 1, surgical device is configured for selective connection with an adapter 410, and, in turn, adapter 410 is configured for selective connection with end effectors 400 or loading units, which may be a single use loading units (“SULU”) or a multiple use loading unit (MULU”). Although described with respect to adapter 410 and end effector 400, different adapters configured for use with different end effectors and/or different end effectors configured for use with adapter 410 are also capable of being used with surgical device 100. Suitable end effectors configured for use with adapter 410 and/or other adapters usable with surgical device 100 include end effectors configured for performing, for example, endoscopic gastro-intestinal anastomosis (EGIA) procedures. Surgical device 100 includes a controller 200, configured to control actuation of the surgical device 100, as well as firing and forming of staples in tissue. The controller 200 may be located on main controller circuit board 142*b* (FIG. 2A) and/or may be external to the surgical device 100.

Figure 2A:
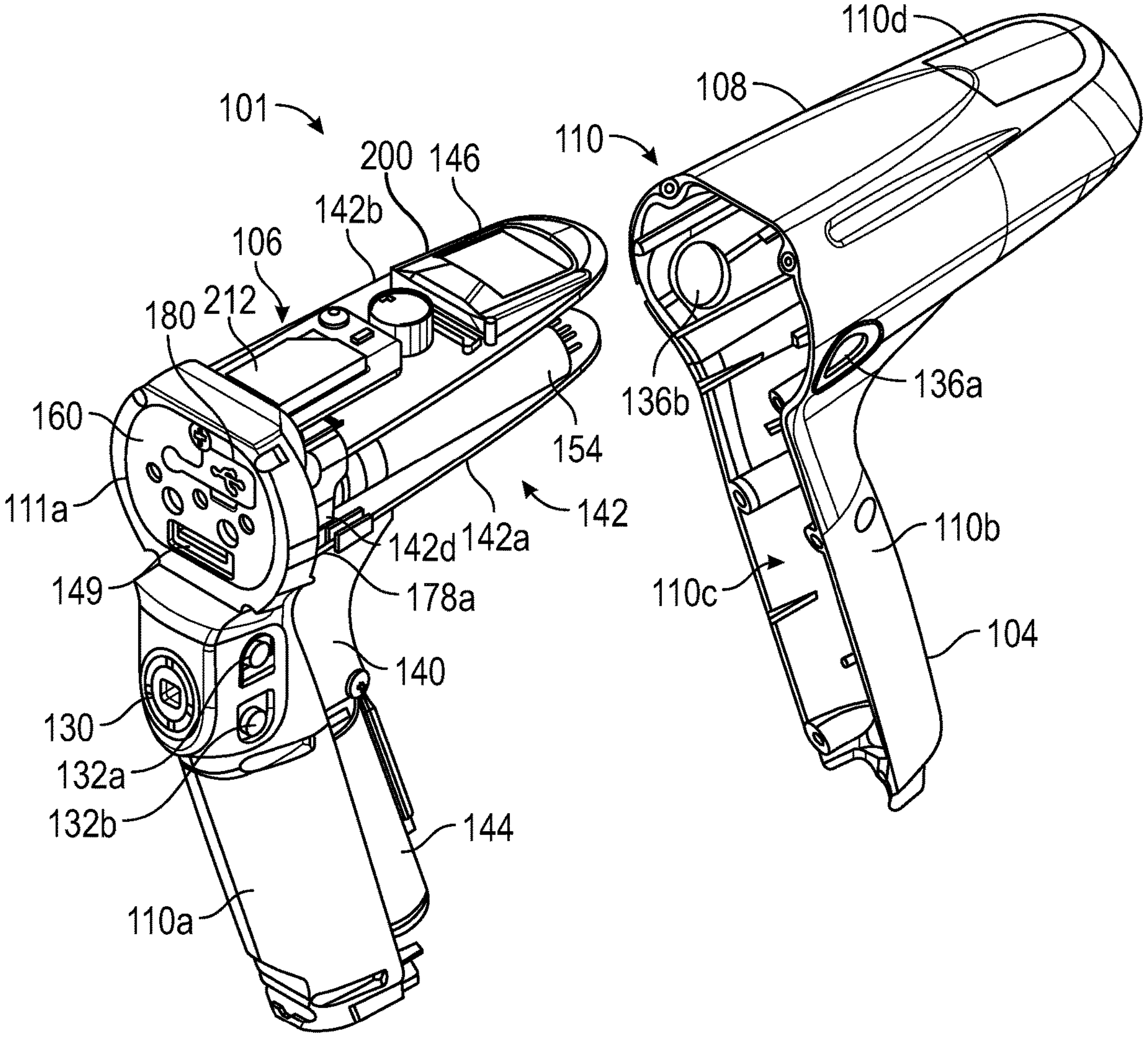
FIG. 2A is a front, perspective view of the power-pack with an inner rear housing separated therefrom.
Figure 2B:
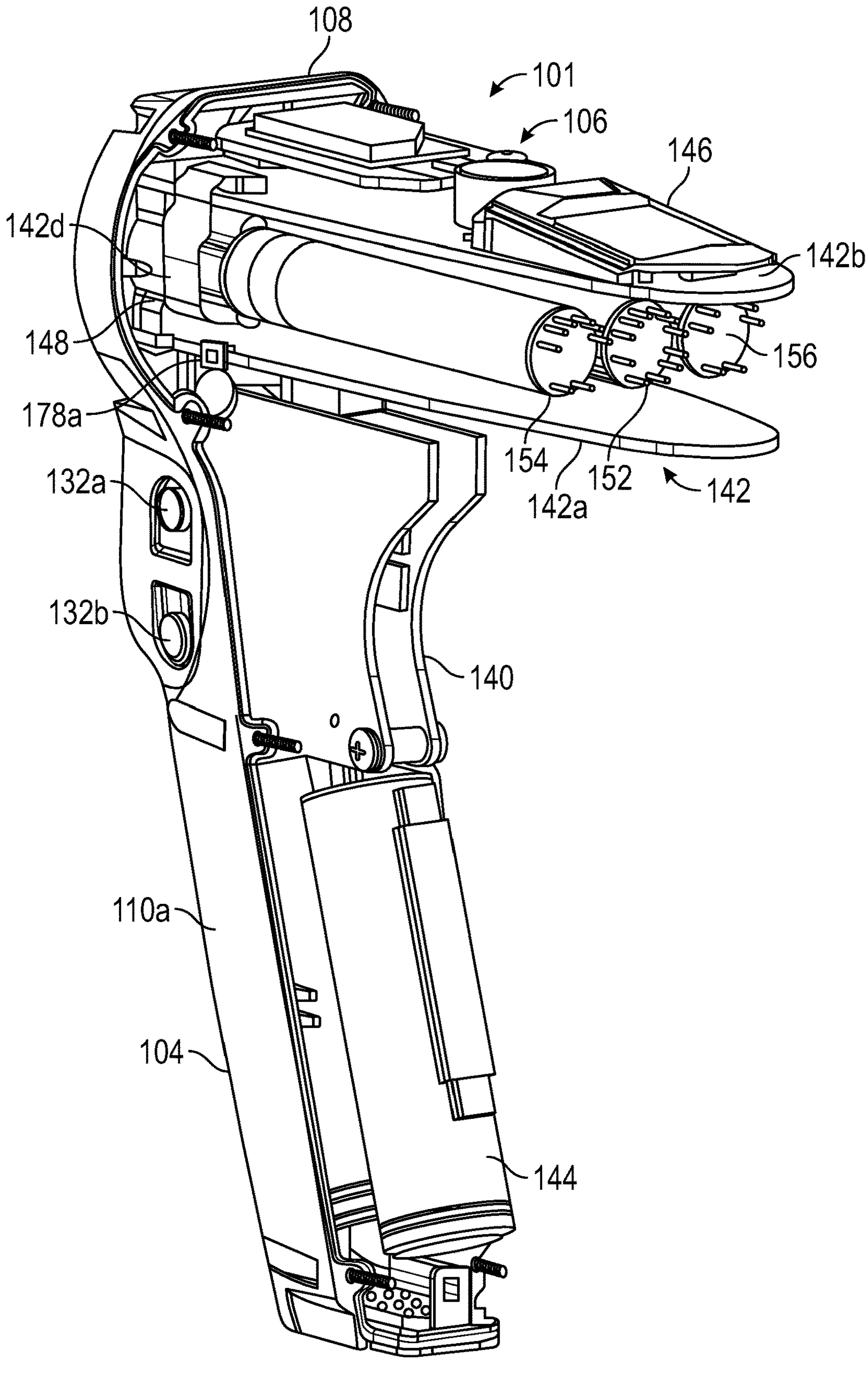
FIG. 2B is a rear, perspective view of the power-pack with the inner rear housing removed therefrom.

With reference to FIGS. 2A and 2B, surgical device 100 includes inner handle housing 110. Inner handle housing 110 provides a housing in which power-pack core assembly 106 is situated. Power-pack core assembly 106 includes a rechargeable battery 144 configured to supply power to any of the electrical components of surgical device 100, a battery circuit board 140, and a controller circuit board 142. Controller circuit board 142 includes a motor controller circuit board 142*a*, a main controller circuit board 142*b*, and a first ribbon cable 142*c* interconnecting motor controller circuit board 142*a* and main controller circuit board 142*b*. The motor controller circuit board 142*a* is communicatively coupled with the battery circuit board 140 enabling communication therebetween and between the battery circuit board 140 and the main controller circuit board 142*b*.

Power-pack core assembly 106 further includes a display screen 146 supported on main controller circuit board 142*b*. Display screen 146 is visible through a clear or transparent window 110*d* (see FIG. 2A) provided in proximal half-section 110*b* of inner handle housing 110. It is contemplated that at least a portion of inner handle housing 110 may be fabricated from a transparent rigid plastic or the like. It is further contemplated that outer shell housing 10 may either include a window formed therein (in visual registration with display screen 146 and with window 110*d* of proximal half-section 110*b* of inner handle housing 110, and/or outer shell housing 10 may be fabricated from a transparent rigid plastic or the like.

Power-pack core assembly 106 further includes a first motor 152, a second motor 154, and a third motor 156 each electrically connected to controller circuit board 142 and battery 144. Motors 152, 154, 156 are disposed between motor controller circuit board 142*a* and main controller circuit board 142*b*. Each motor 152, 154, 156 includes a respective motor shaft 152*a*, 154*a*, 156*a* extending therefrom. Each motor shaft 152*a*, 154*a*, 156*a* has a tri-lobe transverse cross-sectional profile for transmitting rotative forces or torque. As an alternative to motors 152, 154, 156, it is envisioned that more or fewer motors may be provided or that one or more other drive components may be utilized, e.g., a solenoid, and controlled by appropriate controllers. Manual drive components are also contemplated.

Each motor 152, 154, 156 is controlled by a respective motor controller "MC0," MC1," "MC2." Motor controllers "MC0," MC1," "MC2" are disposed on the motor controller circuit board 142*a*. The motor controllers are disposed on motor controller circuit board 142*a* and are, for example, A3930/31K motor drivers from Allegro Microsystems, Inc. The A3930/31K motor drivers are designed to control a 3-phase brushless DC (BLDC) motor with N-channel external power MOSFETs, such as the motors 152, 154, 156. Each of the motor controllers is coupled to a main controller or master chip 157 disposed on the main controller circuit board 142*b* via first ribbon cable 142*c* which connects the motor controller circuit board 142*a* with the main controller circuit board 142*b*. The main controller 157 communicates with motor controllers "MC0," MC1," "MC2" through a field-programmable gate array (FPGA) 162, which provides control logic signals (e.g., coast, brake, etc.). The control logic of motor controllers "MC0," MC1," "MC2" then outputs corresponding energization signals to respective motor 152, 154, 156 using fixed-frequency pulse width modulation (PWM). The main controller 157 is also coupled to memory 165, which is also disposed on the main controller circuit board 142*b*. The main controller 157 is, for example, an ARM Cortex M4 processor from Freescale Semiconductor, Inc, which includes 1024 kilobytes of internal flash memory.

Each motor 152, 154, 156 is supported on a motor bracket 148 such that motor shaft 152*a*, 154*a*, 156*a* are rotatably disposed within respective apertures of motor bracket 148. As illustrated in FIG. 2B, motor bracket 148 rotatably supports three rotatable drive connector sleeves 152*b*, 154*b*, 156*b* that are keyed to respective motor shafts 152*a*, 154*a*, 156*a* of motors 152, 154, 156. Drive connector sleeves 152*b*, 154*b*, 156*b* non-rotatably receive proximal ends of respective coupling shaft 64*a*, 64*b*, 64*c* of plate assembly 60 of outer shell housing 10, when power-pack 101 is disposed within outer shell housing 10. Drive connector sleeves 152*b*, 154*b*, 156*b* are each spring biased away from respective motors 152, 154, 156.

Rotation of motor shafts 152*a*, 154*a*, 156*a* by respective motors 152, 154, 156 function to drive shafts and/or gear components of adapter 410 in order to perform the various operations of surgical device 100. In particular, motors 152, 154, 156 of power-pack core assembly 106 are configured to drive shafts and/or gear components of adapter 410 in order to selectively move tool assembly 404 of end effector 400 relative to proximal body portion 402 of end effector 400, to rotate end effector 400 about a longitudinal axis to move staple cartridge 314 relative to anvil assembly 406 of end effector 400, and/or to fire staples from within staple cartridge 314 of end effector 400.

Motor bracket 148 also supports an electrical adapter interface receptacle 149. Electrical receptacle 149 is in electrical connection with main controller circuit board 142*b* by a second ribbon cable 142*d*. Electrical receptacle 149 defines a plurality of electrical slots for receiving respective electrical contacts or blades extending from pass-through connector 66 of plate assembly 60 of outer shell housing 10.

In use, when adapter 410 is mated to surgical device 100, each coupling shaft 64*a*, 64*b*, 64*c* of plate assembly 60 of outer shell housing 10 of surgical device 100 couples with a corresponding rotatable connector sleeve 218, 220, 222 of adapter 410. In this regard, the interface between corresponding first coupling shaft 64*a* and first connector sleeve 218, the interface between corresponding second coupling shaft 64*b* and second connector sleeve 220, and the interface between corresponding third coupling shaft 64*c* and third connector sleeve 222 are keyed such that rotation of each of coupling shafts 64*a*, 64*b*, 64*c* of surgical device 100 causes a corresponding rotation of the corresponding connector sleeve 218, 220, 222 of adapter 410.

The mating of coupling shafts 64*a*, 64*b*, 64*c* of surgical device 100 with connector sleeves 218, 220, 222 of adapter 410 allows rotational forces to be independently transmitted via each of the three respective connector interfaces. The coupling shafts 64*a*, 64*b*, 64*c* of surgical device 100 are configured to be independently rotated by respective motors 152, 154, 156.

Since each coupling shaft 64*a*, 64*b*, 64*c* of surgical device 100 has a keyed and/or substantially non-rotatable interface with a respective connector sleeve 218, 220, 222 of adapter 410, when adapter 410 is coupled to surgical device 100, rotational force(s) are selectively transferred from motors 152, 154, 156 of surgical device 100 to adapter 410.

The selective rotation of coupling shaft(s) 64*a*, 64*b*, 64*c* of surgical device 100 allows surgical device 100 to selectively actuate different functions of end effector 400. As will be discussed in greater detail below, selective, and independent rotation of first coupling shaft 64*a* of surgical device 100 corresponds to the selective and independent opening and closing of tool assembly 404 of end effector 400, and driving of a stapling/cutting component of tool assembly 404 of end effector 400.

The actuation of push button switch 172*c*, corresponding to a downward actuation of toggle control button 30, causes controller circuit board 142 to provide appropriate signals to motor 152 to close a tool assembly 404 of end effector 400 and/or to fire staples from within staple cartridge 314 of end effector 400.

The actuation of push button switch 172*a*, corresponding to an upward actuation of toggle control button 30, causes controller circuit board 142 to provide appropriate signals to motor 152 to retract a staple sled and open tool assembly 404 of end effector 400.

Figure 3:
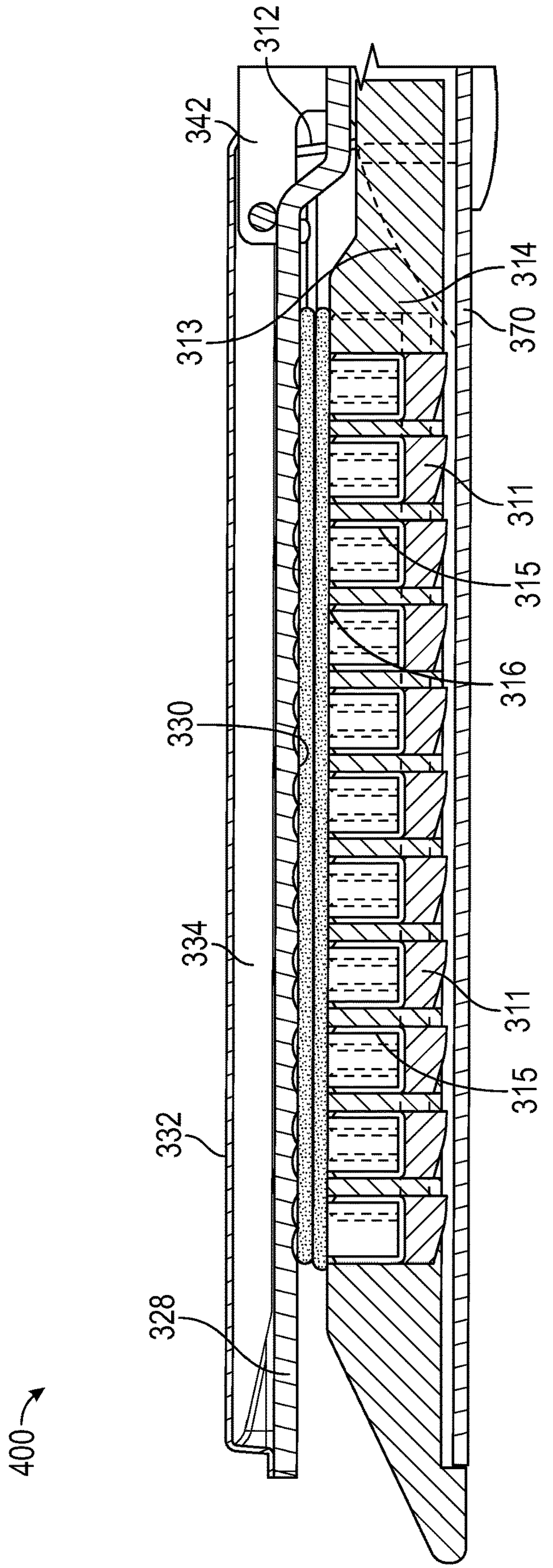
FIG. 3 is a front perspective view of an end effector of the surgical device of FIG. 1.

As illustrated in FIG. 3, end effector 400 of surgical device 100 includes a staple cartridge 314 removably supported in a carrier. The staple cartridge 314 defines a central longitudinal slot 370 defined centrally therealong to receive a knife 312, and a plurality of linear rows of staple retention slots 316 positioned on each side of the longitudinal slot. Each of the staple retention slots 316 receives a single staple 315 and a portion of a staple pusher 311. During operation of surgical device 100, a drive assembly (not shown) actuates a knife 312 that abuts an actuation sled 313 and pushes actuation sled through the cartridge 314. As the actuation sled 313 moves through the cartridge, cam wedges of the actuation sled 313 sequentially engage the staple pushers 311 to move the staple pushers 311 vertically within the staple retention slots 316 and sequentially ejects a single staple therefrom for formation against an anvil plate (not shown).

Figure 4:
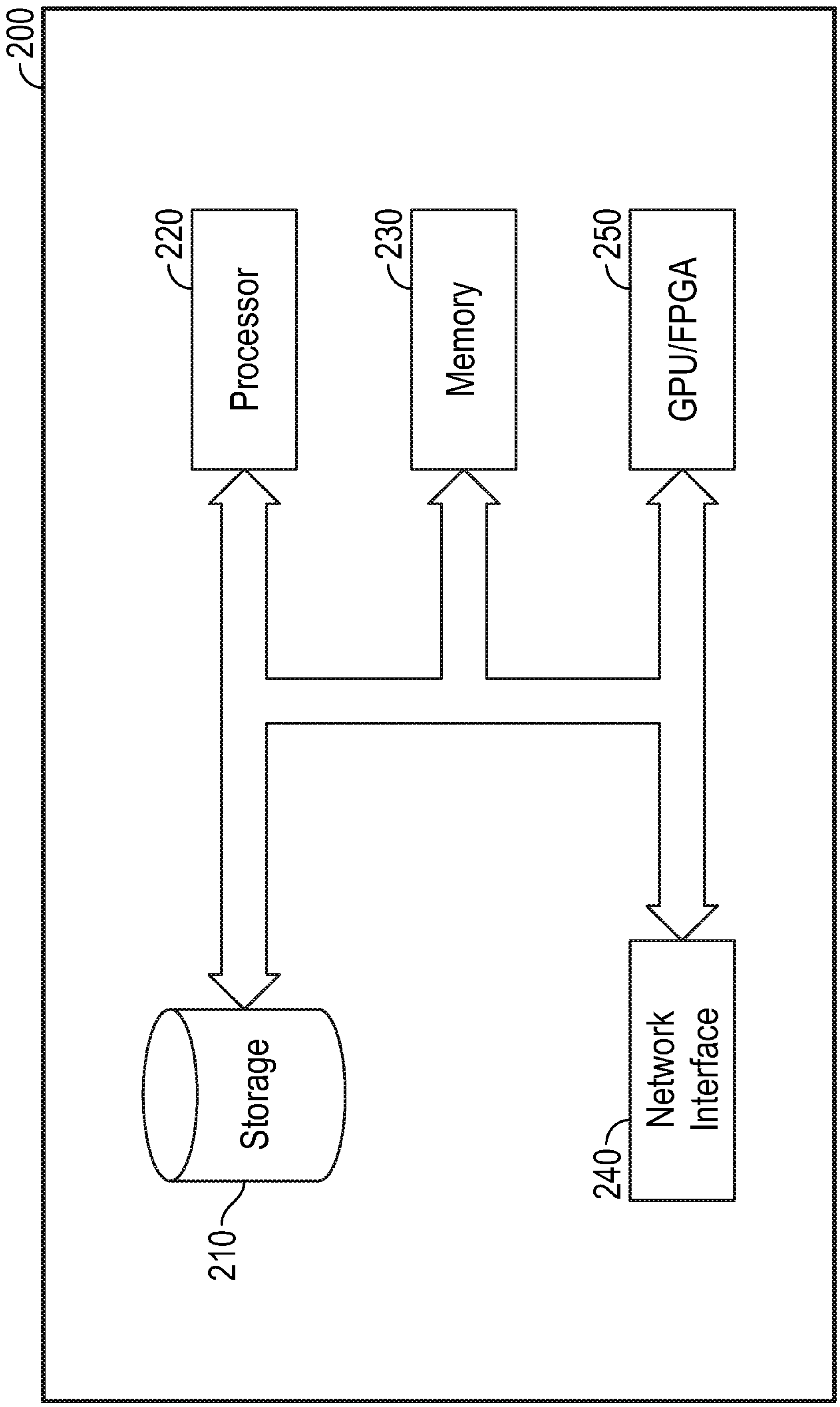
FIG. 4 is a functional block diagram of a controller configured for use with the handheld surgical device and adapter assembly of FIG. 1 in accordance with aspects of the present disclosure.

Now referring to FIG. 4, controller 200 includes a processor 220 connected to a computer-readable storage medium or a memory 230. The computer-readable storage medium or memory 230 may be a volatile type of memory, e.g., RAM, or a non-volatile type of memory, e.g., flash media, disk media, etc. In various aspects of the disclosure, the processor 220 may be another type of processor such as a digital signal processor, a microprocessor, an ASIC, a graphics processing unit (GPU), a field-programmable gate array (FPGA), or a central processing unit (CPU). In certain aspects of the disclosure, network inference may also be accomplished in systems that have weights implemented as memristors, chemically, or other inference calculations, as opposed to processors.

In aspects of the disclosure, the memory 230 can be random access memory, read-only memory, magnetic disk memory, solid-state memory, optical disc memory, and/or another type of memory. In some aspects of the disclosure, the memory 230 can be separate from the controller 200 and can communicate with the processor 220 through communication buses of a circuit board and/or through communication cables such as serial ATA cables or other types of cables. The memory 230 includes computer-readable instructions that are executable by the processor 220 to operate the controller 200. In other aspects of the disclosure, the controller 200 may include a network interface 240 to communicate with other computers or to a server. A storage device 210 may be used for storing data. The disclosed method may run on the controller 200 or on a user device, including, for example, on a mobile device, an IoT device, or a server system.

Figure 5:
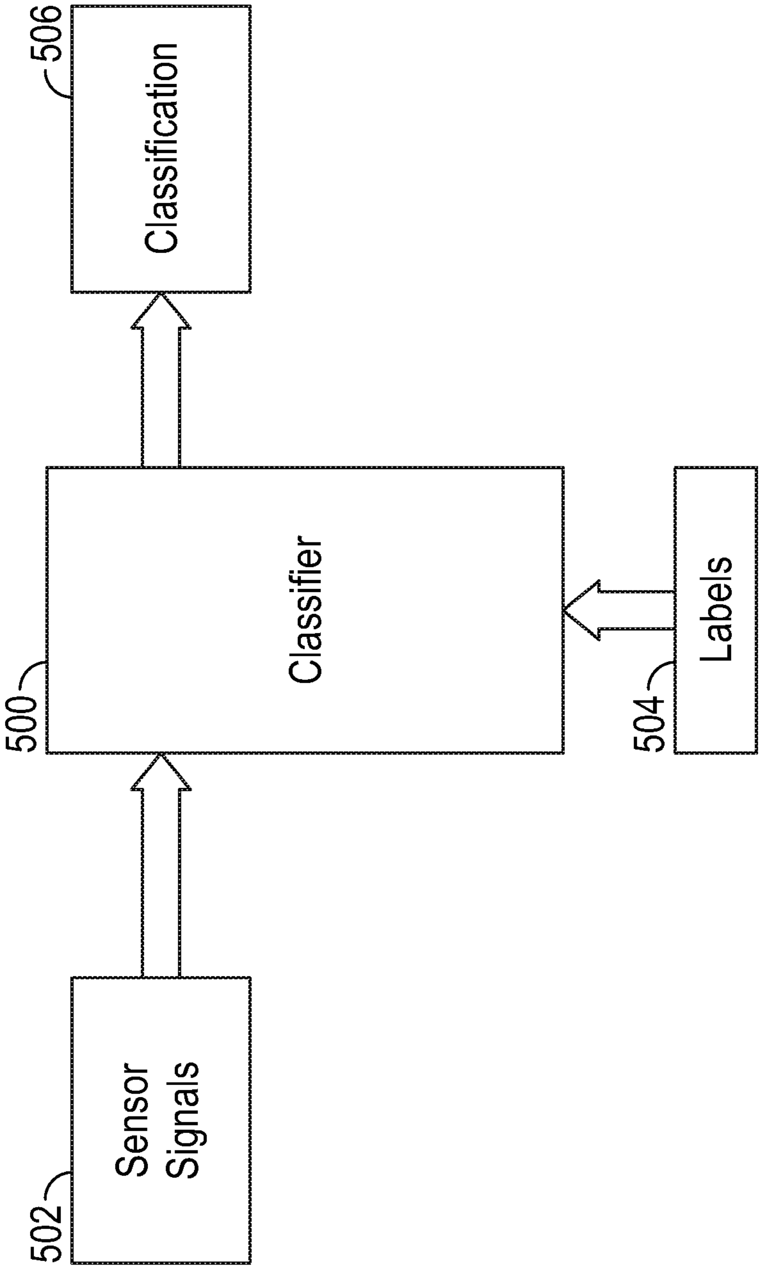
FIG. 5 is a block diagram of a deep learning neural network and inputs and outputs of a deep learning neural network, in accordance with aspects of the disclosure.

With reference to FIG. 5, a block diagram for a machine learning classifier 500 for classifying data in accordance with some aspects of the disclosure is shown. In some systems, a machine learning classifier 500 may include, for example, a convolutional neural network (CNN) and/or a recurrent neural network. A deep learning neural network includes multiple hidden layers. As explained in more detail below, the machine learning classifier 500 may leverage one or more classification models (e.g., CNNs, decision trees, Naive Bayes, k-nearest neighbor) to classify data, sensed by the sensor 212 (see FIG. 2A). The sensor 212 (FIG. 2A), for example, may include an ammeter configured to sense motor current, a strain gauge configured to sense force, an accelerometer, a battery controller, an inertial measurement unit configured to sense angular rate, force and/or magnetic field, an encoder configured to measure motor position and/or motor velocity, a current sense resistor, a hall effects sensor configured to measure motor current, and/or a load cell configured to sense load. The machine learning classifier 500 may be executed on the controller 200 (FIG. 4). Persons skilled in the art will understand the machine learning classifier 500 and how to implement it.

In machine learning, a CNN is a class of artificial neural network (ANN), most commonly applied to analyzing visual imagery. The convolutional aspect of a CNN relates to applying matrix processing operations to localized portions of an image, and the results of those operations (which can involve dozens of different parallel and serial calculations) are sets of many features that are delivered to the next layer. A CNN typically includes convolution layers, activation function layers, deconvolution layers (e.g., in segmentation networks), and/or pooling (typically max pooling) layers to reduce dimensionality without losing too many features. Additional information may be included in the operations that generate these features. Providing unique information that yields features that give the neural networks information can be used to provide an aggregate way to differentiate between different data input to the neural networks.

Figure 6:
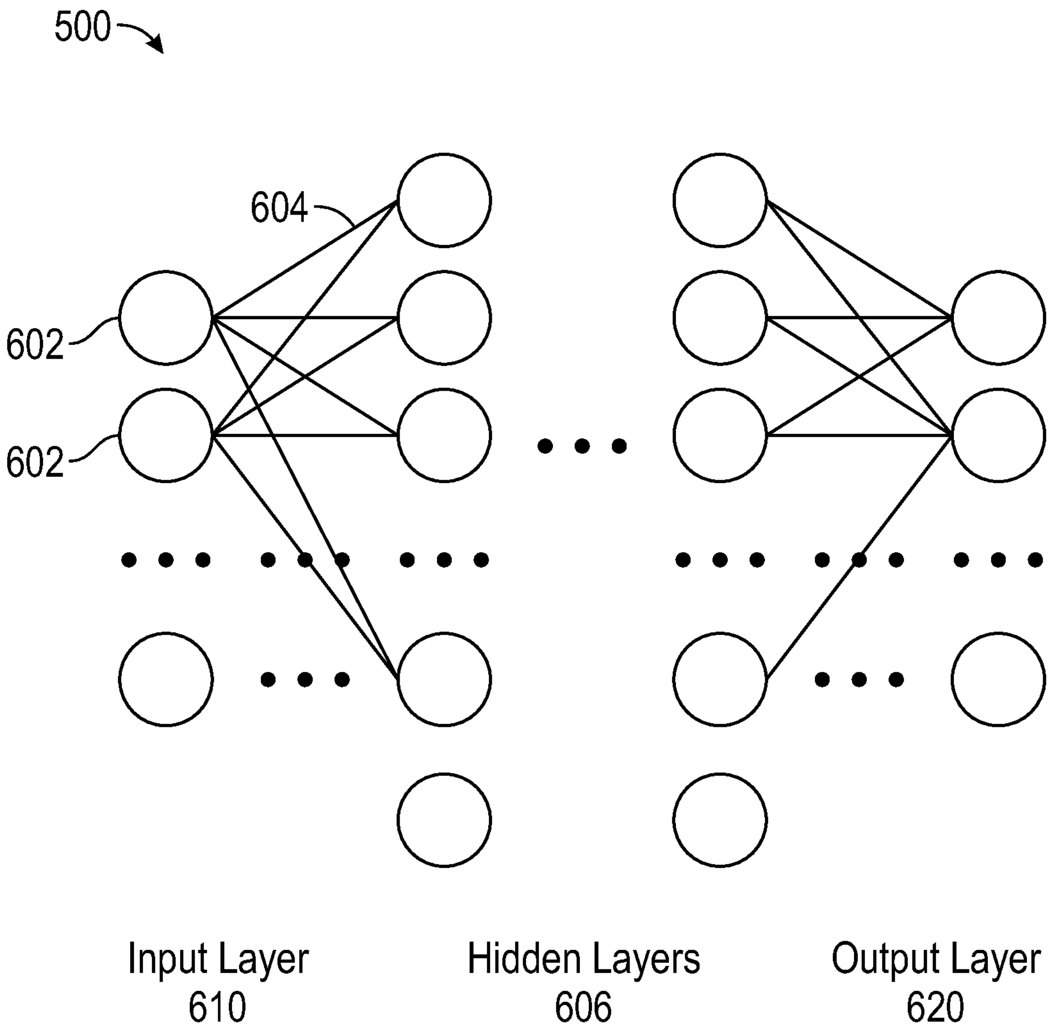
FIG. 6 is a diagram of layers of the deep learning neural network of FIG. 5 in accordance with aspects of the disclosure.

Referring to FIG. 6, generally, a machine learning classifier 500 (e.g., a convolutional deep learning neural network) includes at least one input layer 610, a plurality of hidden layers 606, and at least one output layer 620. The input layer 610, the plurality of hidden layers 606, and the output layer 620 all include neurons 602 (e.g., nodes). The neurons 602 between the various layers are interconnected via weights 604. Each neuron 602 in the deep learning neural network 500 computes an output value by applying a specific function to the input values coming from the previous layer. The function that is applied to the input values is determined by a vector of weights 604 and a bias. Learning, in the deep learning neural network, progresses by making iterative adjustments to these biases and weights. The vector of weights 604 and the bias are called filters (e.g., kernels) and represent particular features of the input (e.g., a particular shape). The machine learning classifier 500 may output logits.

The machine learning classifier 500 may be trained based on labeling training data to optimize weights. For example, sensor may include motor data PWM signal data. In some methods in accordance with this disclosure, the training may include supervised learning. Persons skilled in the art will understand training the machine learning classifier 500 and how to implement it.

In some methods in accordance with this disclosure, the deep learning neural network 500 may be used to classify sensor data captured by the sensor 212 (see FIG. 2A). The classification of the sensor signal 502 may be used to determine classification scores for various predictions 506 for use in determining a point (e.g., end stop point) at which the knife 312 (FIG. 3) of surgical device 100 ceases to cut tissue.

Figure 7:
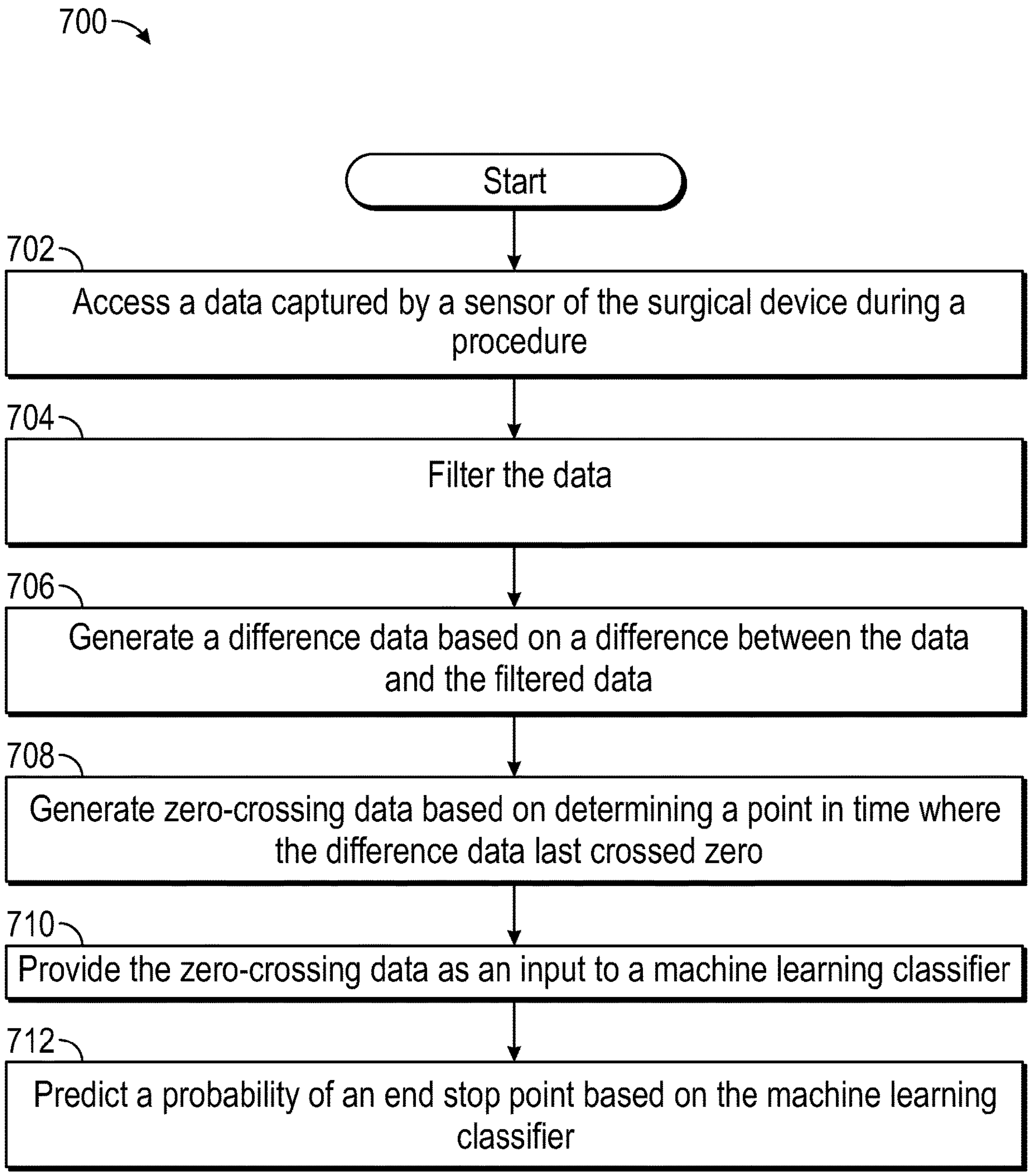
FIG. 7 is a flow diagram of a computer-implemented method for controlling the surgical device of FIG. 1.

Referring to FIG. 7, a computer-implemented method for control of a surgical device is shown. The method may be performed on controller 200 or on a separate device, such as a server or a mobile user device.

The surgical device 100 of FIG. 1 enables a user to perform one handed articulation. Clamp, fire, and retract may also be accomplished with one hand enabling a more stable tissue interaction during firing. The disclosed method has the benefit of reducing undesired motion after the end stop point.

Initially at step 702, the controller 200 accesses raw data captured by a sensor 212 (FIG. 2A) of the surgical device 100 during a procedure. The raw data may represent a time series signal, for example, motor current over time.

Figure 8:
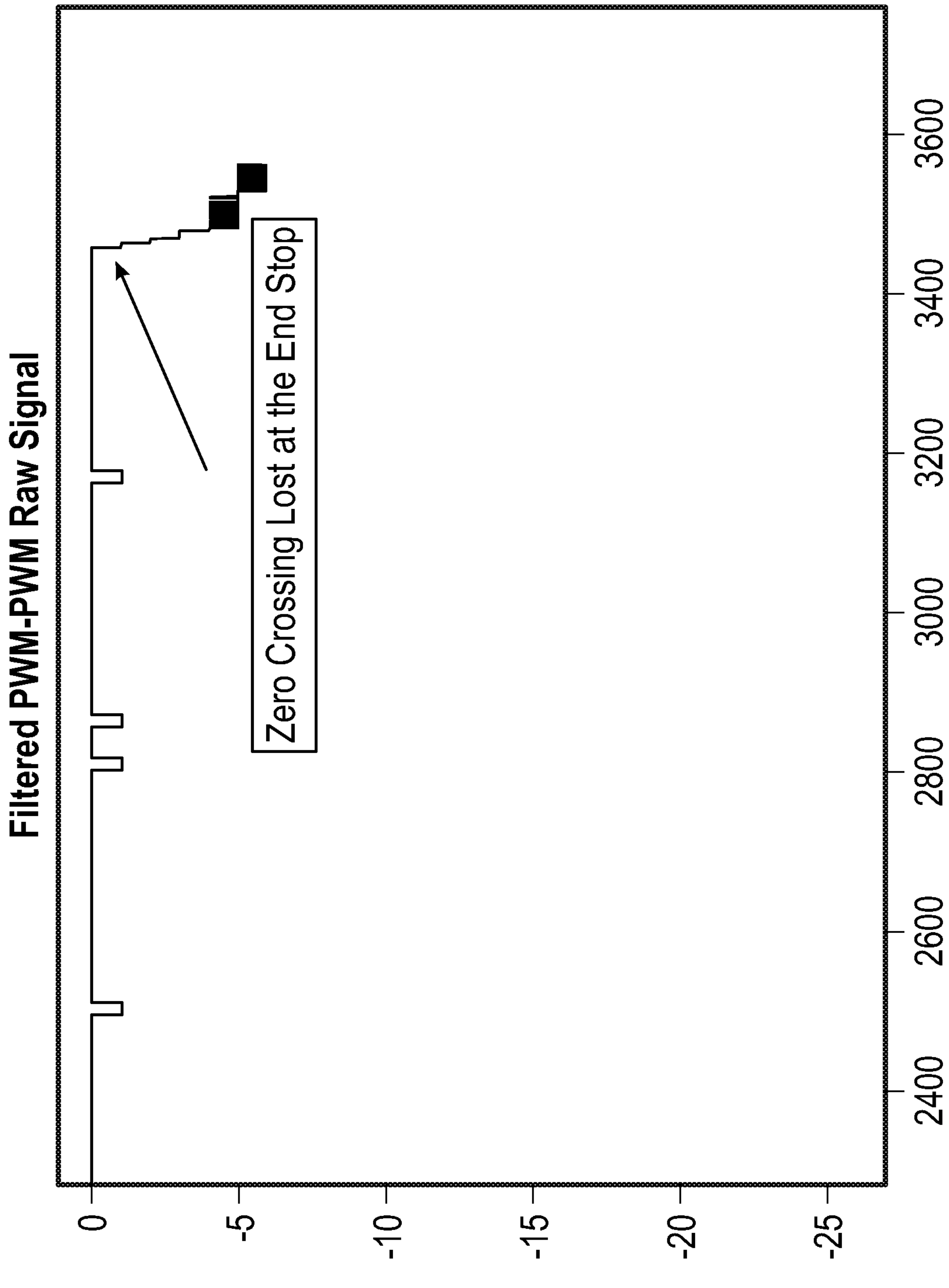
FIG. 8 is a graph of a difference signal generated by detecting a difference between a filtered PWM signal and a raw PWM signal.

For example, the motor 152, 154, 156 (FIG. 2B) advances the knife 312 (FIG. 3) along a staple end effector 400 (FIG. 1). As the knife 312 advances, the knife 312 compresses tissue, deploys staples through the tissue, and cuts between the staples. At the end of the stapling end effector 400, the knife 312 reaches an end stop point and can advance no further. The disclosed method algorithm uses the sensed data from the stapling system of FIG. 1 to determine the end stop point. The knife 312 must reach the end stop point to fully deploy all the staples. However, any extra rotation of the motor beyond the end stop point can cause unwanted motion of the end effector 400. It may be advantageous to stop the motor 152, 154, 156 as close to the end stop point as possible. The end stop point, as used herein, includes a point at which the knife 312 ceases to cut tissue. Motor speed is controlled by a PWM (pulse width modulation) signal. Towards the end of firing, the PWM signal changes drastically (FIG. 8). PWM speed control works by driving the motor with a series of "ON-OFF" pulses and varying the duty cycle, the fraction of time that the output voltage is "ON" compared to when it is "OFF," of the pulses while keeping the frequency constant. The power applied to the motor can be controlled by varying the width of these applied pulses and thereby varying the average DC voltage applied to the terminals of the motors. By changing or modulating the timing of these pulses, the speed of the motor can be controlled, e.g., the longer the pulse is "ON," the faster the motor will rotate, and likewise, the shorter the pulse is "ON," the slower the motor will rotate. The wider the pulse width, the more average voltage applied to the motor terminals, the stronger the magnetic flux inside the armature windings, and the faster the motor will rotate.

Next, at step 704, the controller 200 filters the raw data. The filter includes a moving minimum filter. For example, a moving minimum filter may be applied to the PWM signal. A moving minimum filter returns an array of local k-point centered minimum values, where each minimum is calculated over a sliding window of length k across neighboring elements.

Next, at step 706, the controller 200 generates a difference data based on a difference between the raw data and the filtered data. For example, a difference is determined between the filtered PWM signal and the raw unfiltered PWM signal.

Next, at step 708, the controller 200 generating zero-crossing data based on determining a point in time where the difference data last crossed zero. A zero-crossing is a point where the sign of a mathematical function changes (e.g., from positive to negative), represented by an intercept of the axis (zero value) in the graph of the function. The point in time may correlate to a physical location where a knife 312 of the surgical device 100 ceases to cut tissue.

For example, a zero-crossing detector is applied on the resultant difference signal. It is observed that at the end point, the signal no longer crosses zero and the corresponding time information is saved as well (FIG. 10). In addition to the zero-crossing feature, several other signal features, such as RMS value, shape factor (FIG. 9), and/or crest factor (FIG. 11) may be extracted as well. Firing data with an end point has a different shape for all of the above features as compared to firing data with no end point.

Next, at step 710, the controller 200 provides the zero-crossing data as an input to a machine learning classifier 500 (FIG. 5). The zero-crossing data includes a time difference between consecutive zero crossing points. For example, features such as the generating zero-crossing data, RMS value, shape factor, and/or crest factor may be used as an input to a decision tree.

Next, at step 712, the machine learning classifier 500 predicts a probability of an end stop point based on the machine learning classifier 500. Time series signal data may be used to train the machine learning classifier 500. Firing data from various configuration may be used.

In aspects, the controller 200 may control the motor 152, 154, 156 to prevent further movement of the surgical device 100.

The controller 200 may determine a safety and/or efficacy of end effector 400 of the surgical device 100 based on the predicted probability. For example, if the predicted probability is above a threshold value, the end effector 400 may be determined to be safe.

In aspects, controller 200 may determine if staples are formed based on the predicted end stop point probability. For example, if the predicted end stop point probability is less than a predetermined number (e.g., less than about 40 percent), the controller may determine that staples are not formed.

Figure 9:
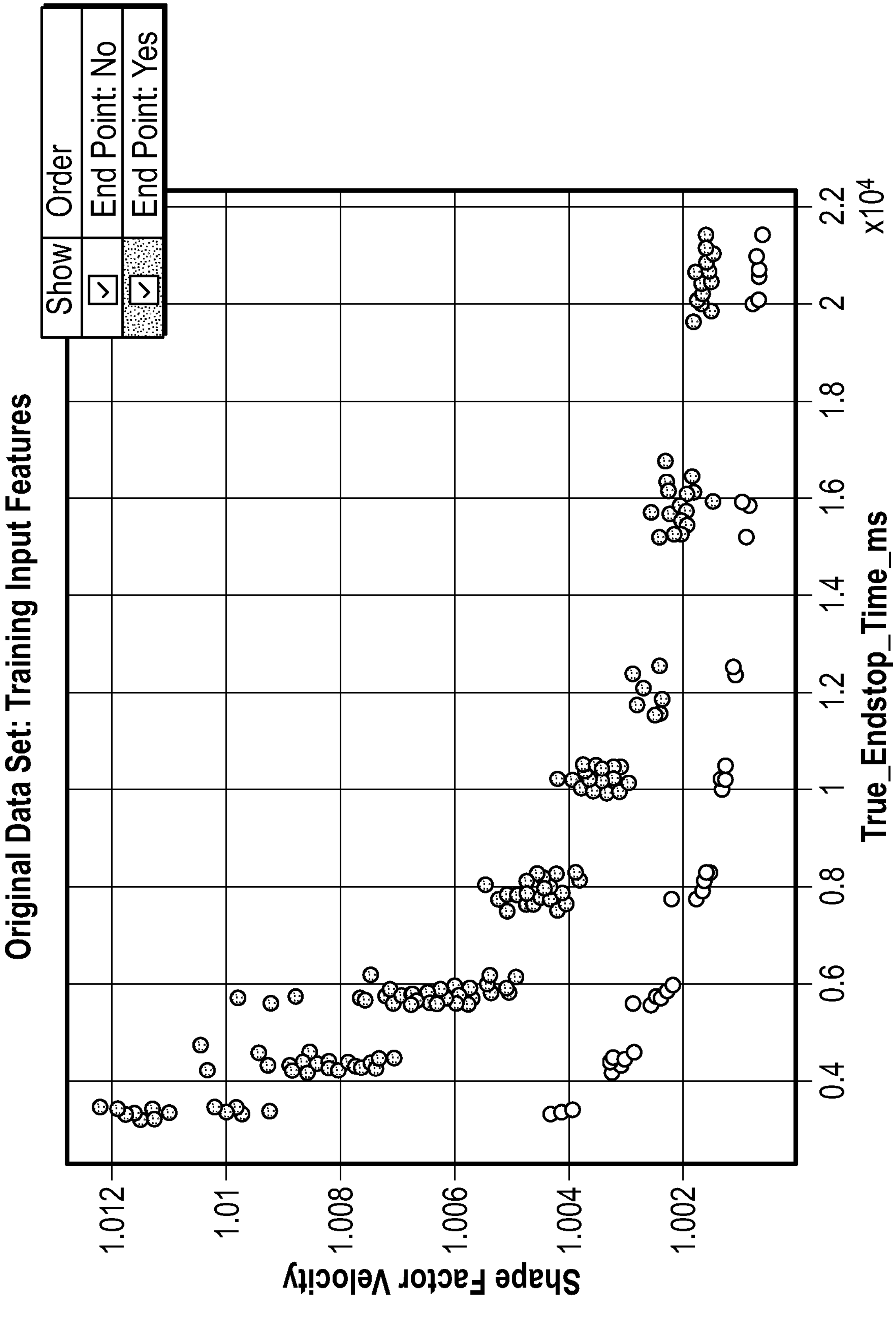
FIG. 9 is graph of a training dataset illustrating shape factor velocity vs. end stop time data with and without end points.
Figure 10:
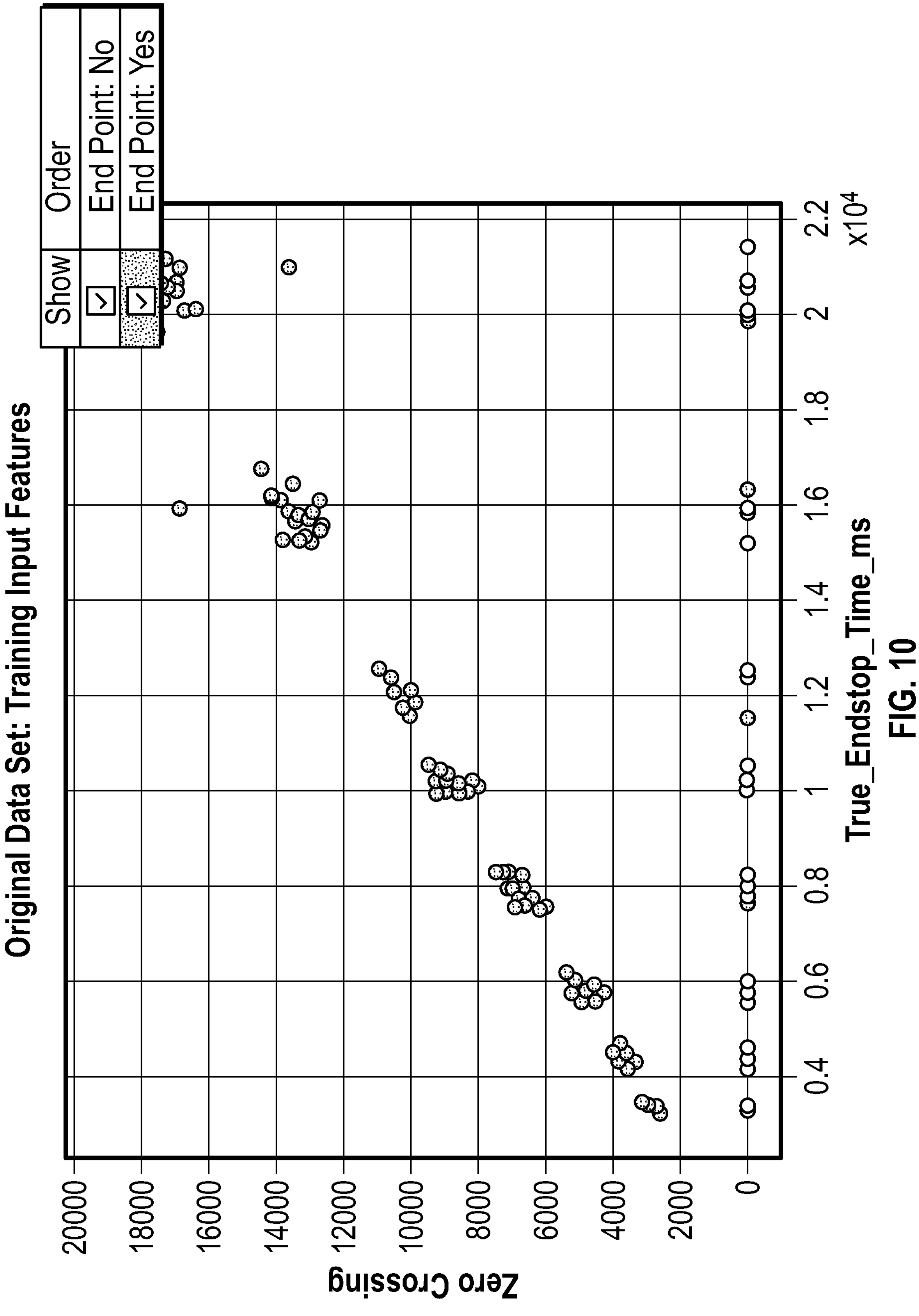
FIG. 10 is graph of a training dataset illustrating zero-crossing vs. end stop time data with and without end points.
Figure 11:
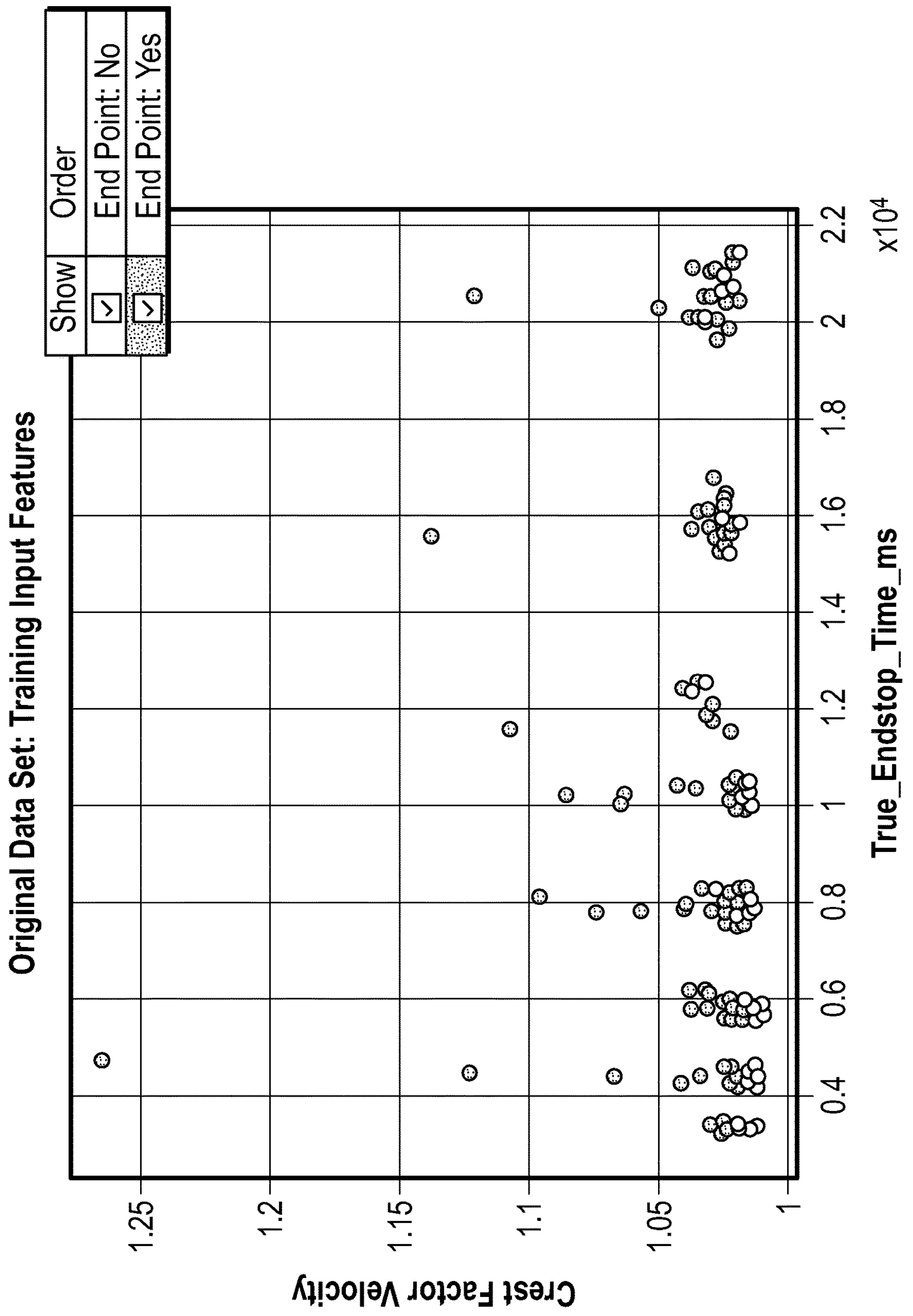
FIG. 11 is graph of a training dataset illustrating crest factor vs. end stop time data with and without end points.

Referring to FIG. 9, a graph of a training dataset illustrating shape factor velocity vs. end stop time data is shown. The plot includes data both with and without end points. FIG. 10 shows a graph of a training dataset illustrating zero-crossing vs. end stop time data. With reference to FIG. 11 a graph of a training dataset illustrating crest factor vs. end stop time data is shown.

Figure 12:
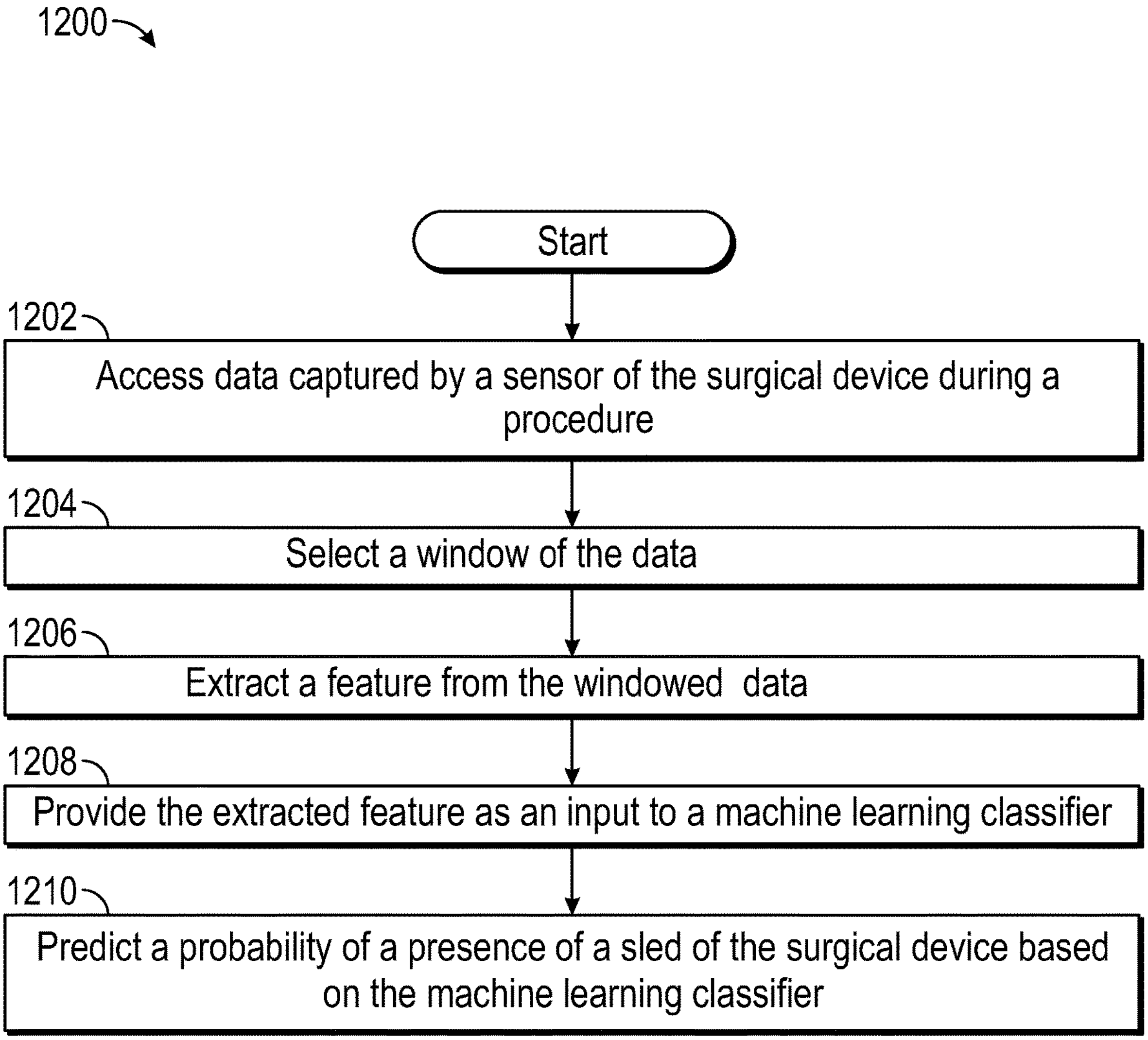
FIG. 12 is a flow diagram of a computer-implemented method for controlling the surgical device of FIG. 1.
Figure 13:
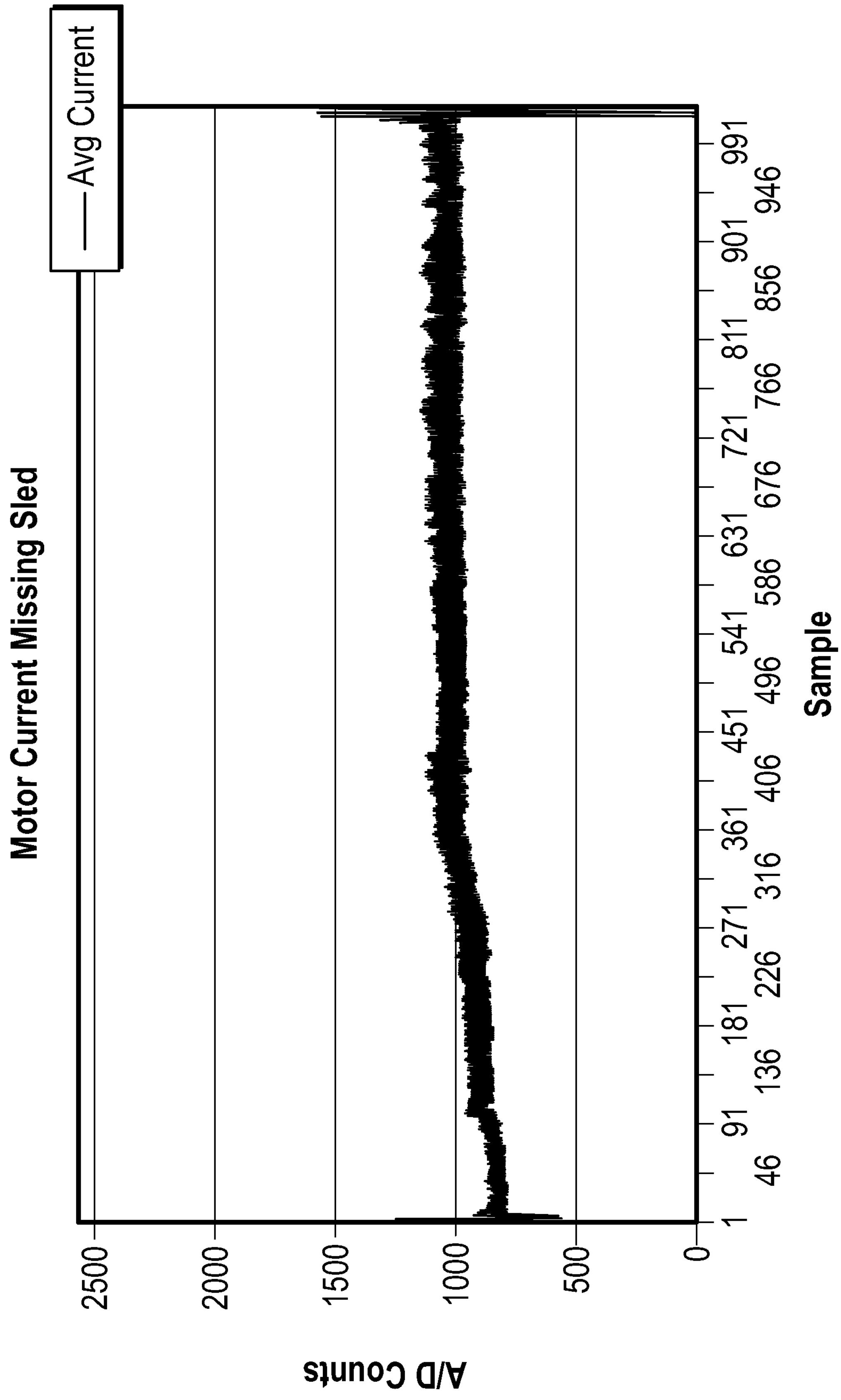
FIGS. 13-15 are graphs of the firing motor current where a sled is missing from the surgical device.
Figure 14:
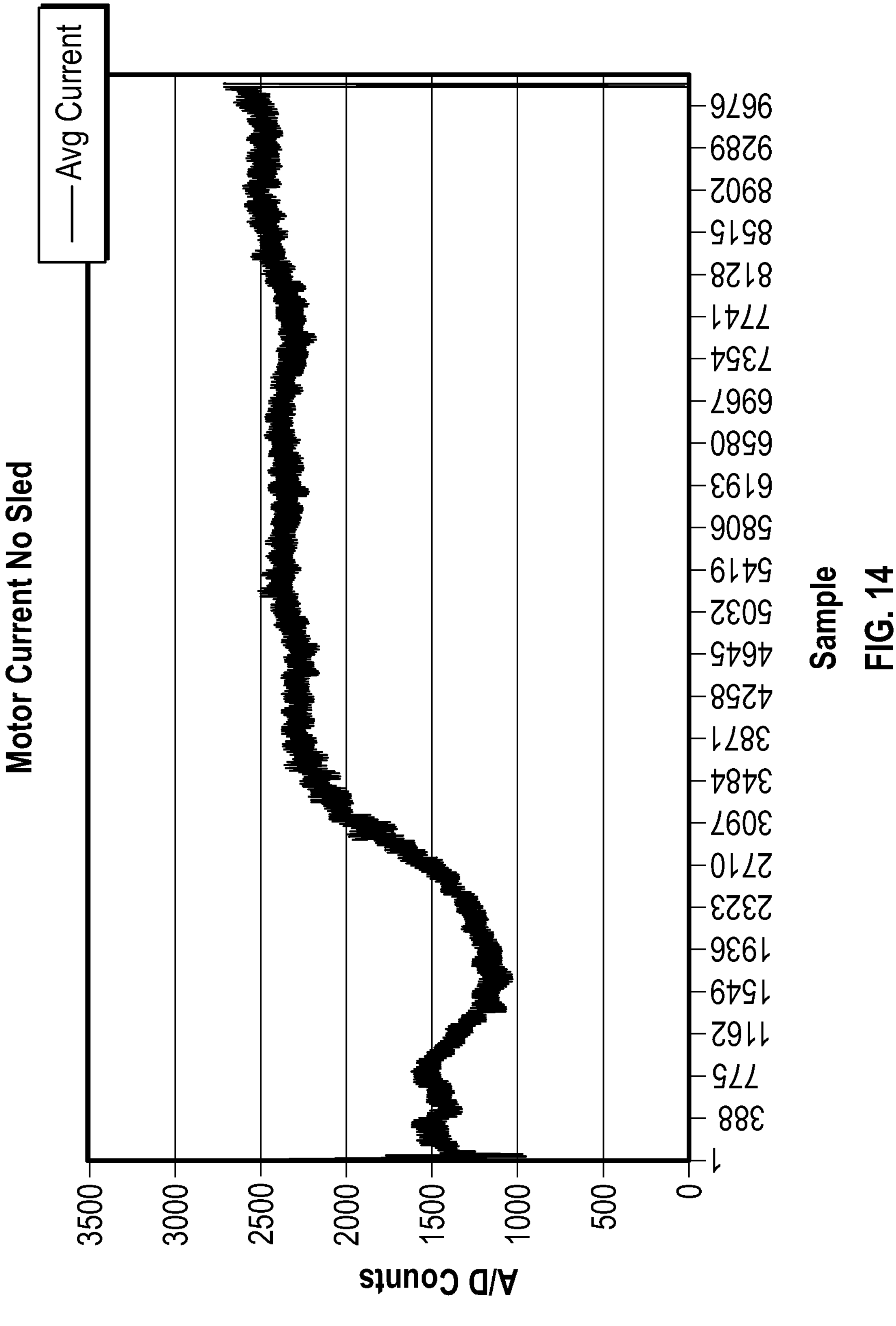
Figure 15:
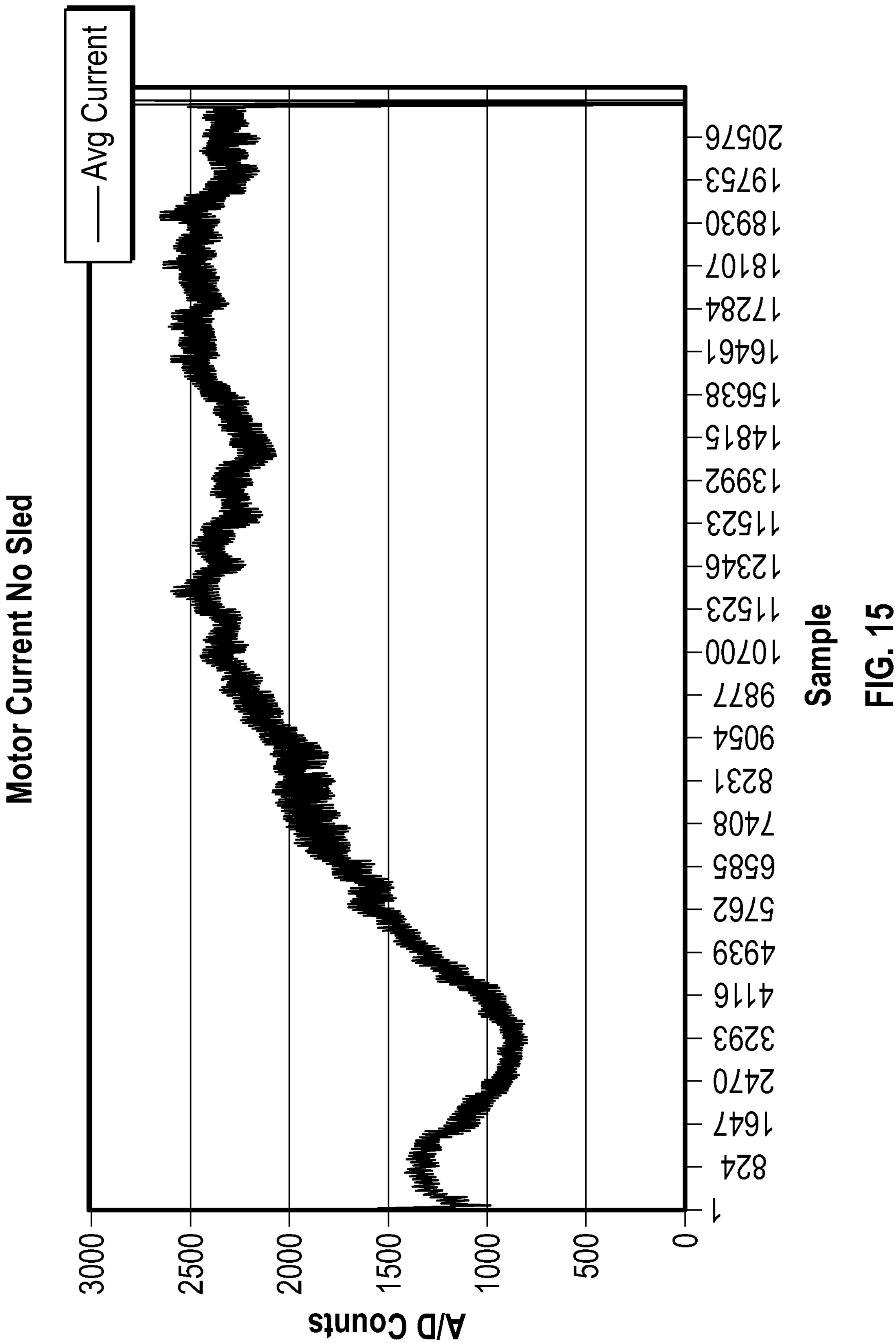
Figure 16:
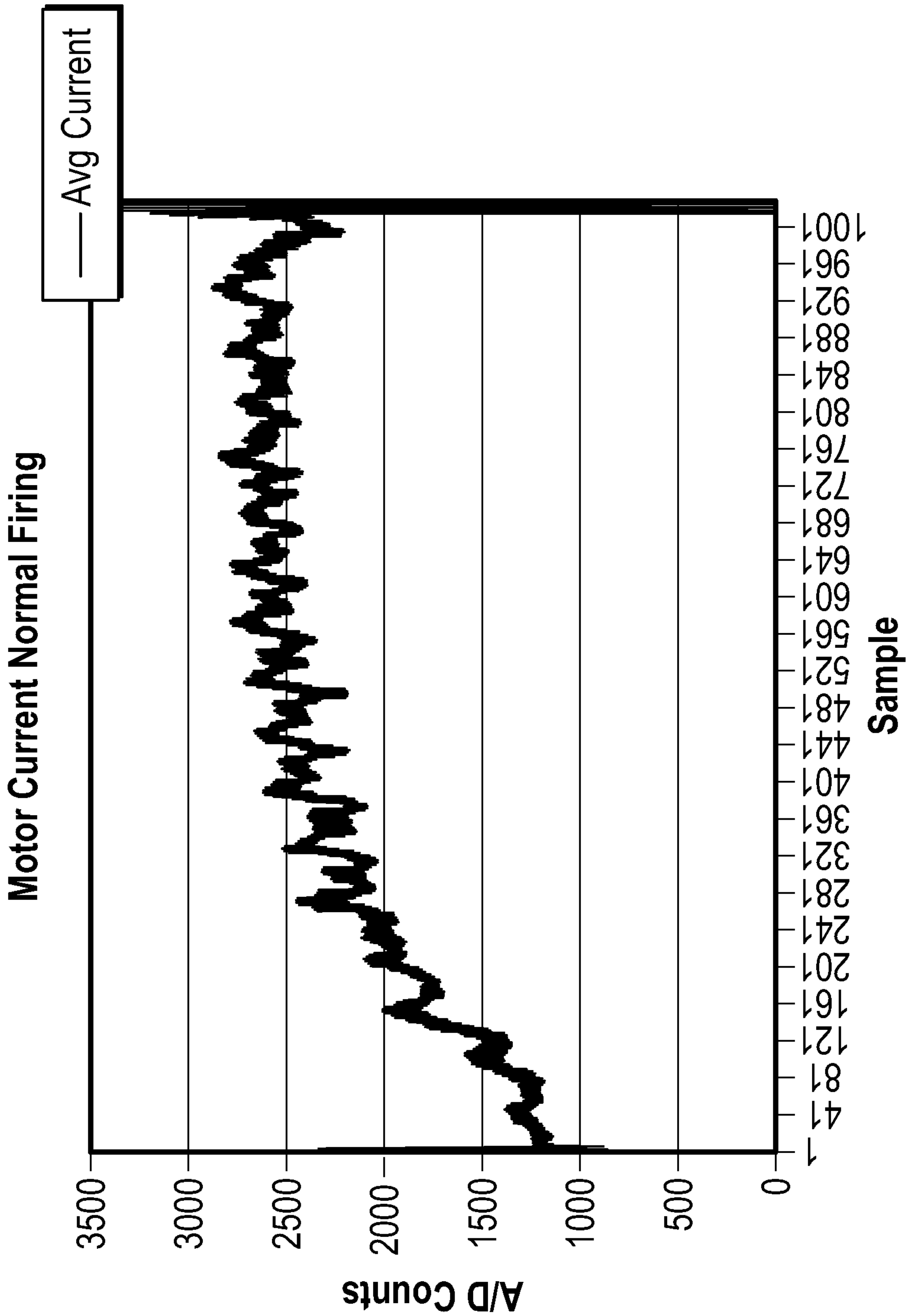
FIG. 16 is a graph of the firing motor current with a sled is present in the surgical device.

Referring to FIG. 12, a computer implemented method for controlling a stapling device 100 of FIG. 1 is shown. In traditional stapler reloads, a possible malfunction is when the device cuts tissue without sealing tissue. The most common way for this to occur is if the stapling SULU is manufactured without the sled 313 (FIG. 17) which activates the staple pushers. The controller 200 collects data on over approximately 250 device use parameters. Device parameters may include, for example, the velocity of the motor, the position, force, type of reload/adapter, age of the instrument, and/or battery readings. A visual difference in the data can be seen when firing a SULU that is forming staples versus one that is not. However, the data may vary depending on the use of the stapler, such as articulation angle, the tissue being firing on, motor current, and/or firing force (FIG. 13-16). This variability in the data makes it difficult to accurately detect the differences between both occurrences using a traditional software algorithm. The disclosed method enables the use of machine learning to classify the signal properties recorded in the surgical device 100 by the controller 200 to detect the presence of sled 313 (FIG. 3).

Initially, at step 1202, the controller 200 accesses raw data (e.g., a dataset) captured by a sensor of the surgical device during a procedure. The sensor 212 (FIG. 2A) may include an ammeter configured to sense motor current, a strain gauge configured to sense force, an accelerometer, a battery controller, and/or an inertial measurement unit configured to sense angular rate, force and/or magnetic field.

Next, at step 1204, the controller 200 selects a window of the raw data. The window is configured to make the raw data non-periodic. For example, a small window of the dataset may be taken, to make a signal finite rather than periodic in nature. This small window of data will also enable bit-by-bit signal processing with overlapping regions. In aspects, window size and/or overlap percentage may be varied and/or optimized. The window size may be optimized based by striking balance between computing efficiency and accuracy.

The window size multiplied by the sampling rate gives the number of samples of data used to formulate a classification decision. The window increment multiplied by the sampling rate gives the number of new samples for each successive analysis. The overlap percentage is optimized by classification error and inference delay.

Next, at step 1206, the controller 200 extracts a feature from the windowed data. A feature represents a recognizable measurement and distinguishing functional component obtained from a section of a pattern. Extracted features may enable reducing the loss of key information embedded in the signal.

A recursive feature elimination (RFE) technique may be used to select information rich features. RFE is a feature selection method that fits a model and removes the weakest feature (or features) until the specified number of features is reached. Features may be ranked by the model's feature importance attributes, and by recursively eliminating a small number of features per loop, RFE attempts to eliminate dependencies and collinearity that may exist in the model.

Next, at step 1208, the controller 200 provides the extracted feature as an input to a machine learning classifier. For example, by using RFE, the average motor current (FIGS. 13-16), motor ticks for position (by an encoder), rotations per minute (RPM), and/or strain gage readings may be selected to feed to the machine learning classifier 500.

Next, at step 1210, the controller 200 predicts a probability of a presence of a sled 313 (FIG. 3) of the surgical device 100 based on the machine learning classifier 500 (FIG. 5). For example, for the classification, a gradient boost machine (GBM) may be used. A GBM is an ensemble of classification tree models. The ensemble of classification tree models are forward-learning ensemble methods that obtain predictive results using gradually improved estimations. Boosting is a flexible nonlinear regression procedure that helps improve the accuracy of trees. Weak classification algorithms are sequentially applied to the incrementally changed data to create a series of decision trees, producing an ensemble of weak prediction models. The output of this classification algorithm is a probability score, this score is fed to an inference layer.

In aspects, the controller 200 may make an inference based on the probability score, and this inference may used to make necessary decisions within the surgical device 100 (FIG. 1). The threshold of probability score may be set in the inference layer as a decision boundary.

The disclosed method has the benefit of enabling the ability to detect the presence of sled in the end effector 400 under broader variable conditions. Another benefit of the disclosed method is the ability to learn and adapt to new environments with a software update leveraging offline learning at research centers.

In aspects, the controller 200 may determining the presence of a sled 313 (FIG. 3) of the surgical device 100 (FIG. 1) based on the predicted probability and in a case that a sled is not determined to be present, disabling firing of the surgical device 100. The controller 200 may provide an indication that a sled 313 is not present based on the determination. For example, the indication may be an audio or visual alert. In aspects, the controller 200 may determine at least one of a safety and/or efficacy of an end effector 400 (FIG. 1) of the surgical device based on the predicted probability.

Figure 17:
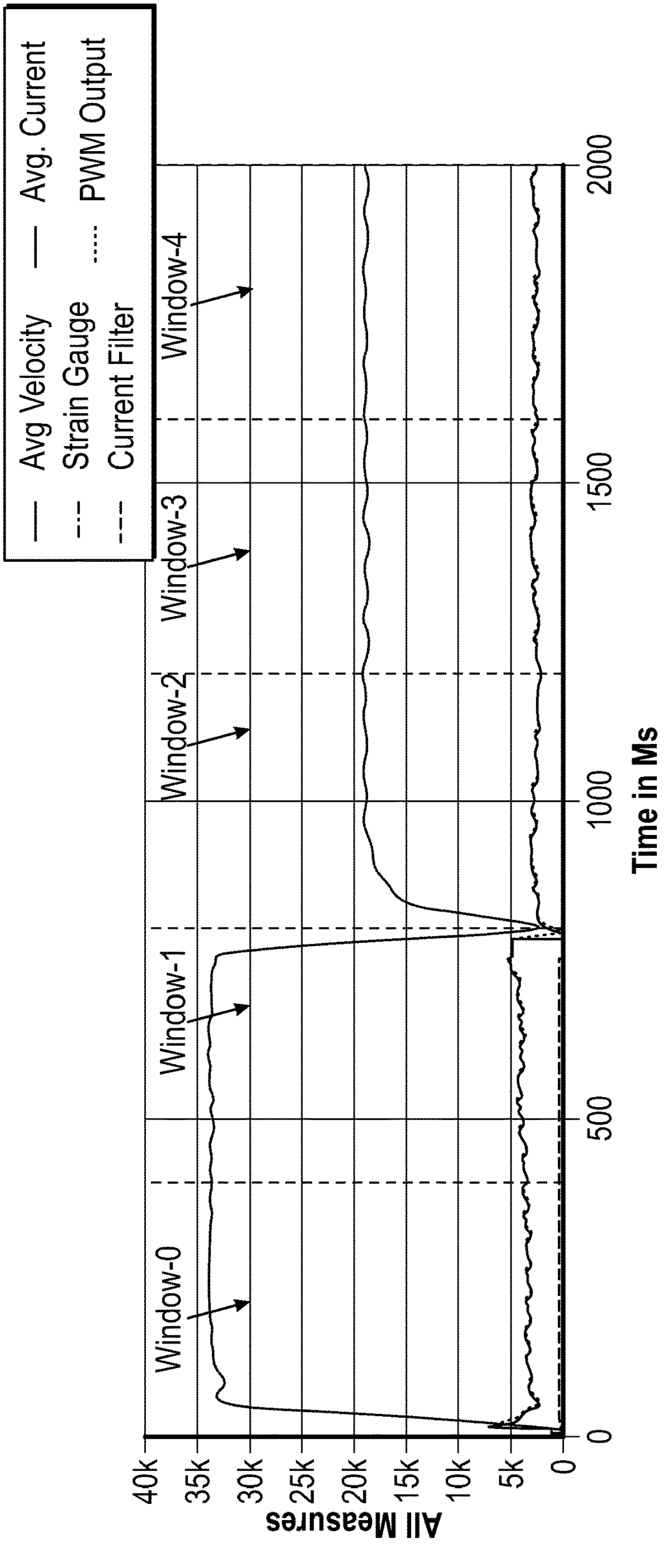
FIG. 17 is a graph of windowed sensor data with a sled present in the surgical device of FIG. 1.
Figure 18:
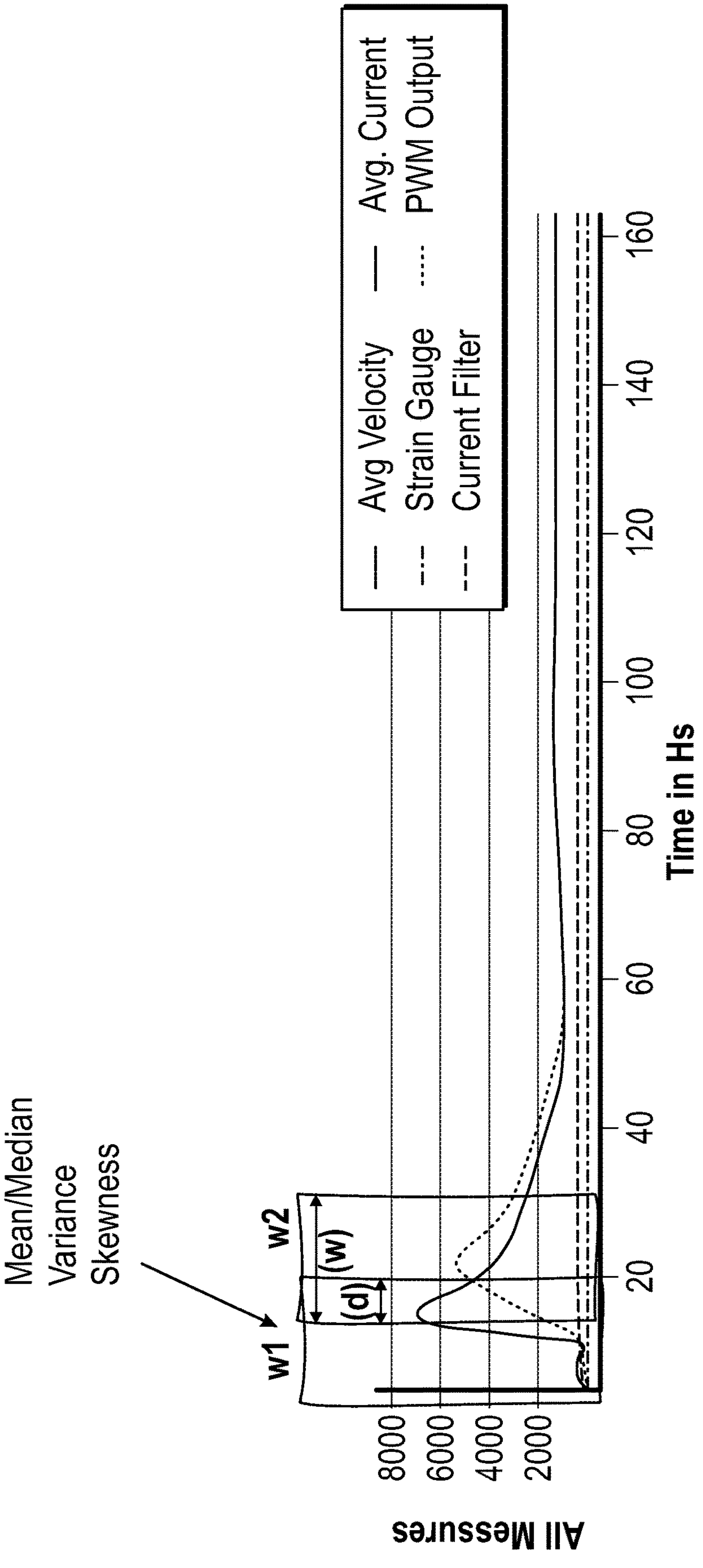
FIG. 18 is a graph of windowed sensor data without a sled present in the surgical device of FIG. 1.

Referring to FIG. 17, a graph of windowed sensor data with a sled present in the surgical device 100 of FIG. 1 is shown. FIG. 18 shows a graph of windowed sensor data without a sled present in the surgical device of FIG. 1.

While illustrated as being used in a handheld surgical device, it is contemplated, and within the scope of the present disclosure for the disclosed systems and methods to be configured for use with various electromechanical and/or electrosurgical instruments and systems. For example, the disclosed methods may be utilized in robotic surgical systems, such as the robotic surgical system shown and described in U.S. Pat. No. 8,828,023, the entire content of which is incorporated herein by reference. In particular, the various aspects disclosed herein may be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients. For a detailed description of exemplary medical work-stations and/or components thereof, reference may be made to U.S. Patent Application Publication No. 2012/0116416, and PCT Application Publication No. WO2016/025132, the entire contents of each of which are incorporated by reference herein.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a surgical device or robotic surgical system.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Persons skilled in the art will understand that the structures and methods specifically described herein and shown in the accompanying figures are non-limiting exemplary aspects, and that the description, disclosure, and figures should be construed merely as exemplary of particular aspects. It is to be understood, therefore, that the present disclosure is not limited to the precise aspects described, and that various other changes and modifications may be effected by one skilled in the art without departing from the scope or spirit of the disclosure. Additionally, the elements and features shown or described in connection with certain aspects may be combined with the elements and features of certain other aspects without departing from the scope of the present disclosure, and that such modifications and variations are also included within the scope of the present disclosure. Accordingly, the subject matter of the present disclosure is not limited by what has been particularly shown and described.

What is claimed is:

1. A computer-implemented method for control of a surgical device, the computer-implemented method comprising:

accessing raw data captured by a sensor of the surgical device during a procedure;

filtering the raw data with a filter to define filtered data, wherein the filter includes a moving minimum filter;

generating a difference data based on a difference between the raw data and the filtered data;

generating zero-crossing data based on determining a point in time where an amplitude of the difference data last crossed from a first non-zero amplitude value, through a zero-amplitude value, to a second non-zero amplitude value with an opposite sign of the first non-zero amplitude value;

providing the zero-crossing data as an input to a machine learning classifier; and predicting a probability of an end stop point based on the machine learning classifier, wherein the end stop point includes a point in time where a knife of the surgical device ceases to cut tissue.

2. The computer-implemented method of claim 1, wherein the raw data includes a PWM signal configured to control a motor of the surgical device.

3. The computer-implemented method of claim 2, further comprising controlling the motor to prevent further movement of the surgical device.

4. The computer-implemented method of claim 1, wherein the difference data includes time series data.

5. The computer-implemented method of claim 1, further comprising determining at least one of a safety or efficacy of an end effector of the surgical device based on the probability of the end stop point.

6. The computer-implemented method of claim 1, further comprising determining if staples of the surgical device are formed based on the probability of the end stop point.

7. The computer-implemented method of claim 1, further comprising determining a presence of a sled of the surgical device based on the end stop point probability.

8. The computer-implemented method of claim 1, further comprising:

processing the difference data to determine at least one of a root means square value, a shape factor, or a crest factor of the difference data; and inputting, to the machine learning classifier, the determined at least one of the root means square value, the shape factor, or the crest factor of the difference data.

9. The computer-implemented method of claim 1, wherein the machine learning classifier includes a decision tree.

10. A system for control of a surgical device, the system comprising:

a surgical stapling device including:

a sensor configured to sense a signal, the signal configured to control a motor of the surgical stapling device;

an end effector comprising a knife configured to cut tissue;

at least one processor; and at least one memory including instructions stored thereon which, when executed by the at least one processor, cause the system to:

access raw data captured by the sensor of the surgical device during a procedure wherein the knife advances through the tissue;

filter the raw data to define filtered data, the filter including a moving minimum filter;

generate a difference data based on a difference between the raw data and the filtered data;

generate zero-crossing data based on determining a point in time where an amplitude of the difference data last crossed from a first non-zero amplitude value, through a zero-amplitude value, to a second non-zero amplitude value with an opposite sign of the first non-zero amplitude value;

input the zero-crossing data to a machine learning classifier; and predict a probability of an end stop point based on the machine learning classifier, wherein the end stop point includes a point in time where the knife of the surgical device ceases to cut tissue.

11. The system of claim 10, wherein the surgical stapling device further comprises a motor configured to advance the knife; wherein the raw data includes a pulse width modulated signal configured to control the motor of the surgical stapling device.

12. The system of claim 10, wherein the instructions, when executed by the at least one processor, further cause the system to determine at least one of a safety or efficacy of the end effector of the surgical stapling device based on the probability of the end stop point.

13. The system of claim 10, wherein the instructions, when executed by the at least one processor, further cause the system to determine if staples of the surgical stapling device are formed based on the probability of the end stop point.

14. The system of claim 10, wherein the instructions, when executed by the at least one processor, further cause the system to:

process the difference data to determine at least one of a root means square value, a shape factor, or a crest factor of the signal; and input to the machine learning classifier the determined at least one of the root means square value, the shape factor, or the crest factor of the signal.

* * * * *